United States Patent [19]

Handa et al.

[11] Patent Number: 4,996,358

[45] Date of Patent: Feb. 26, 1991

[54] HYDROXYLAMINE BEARING AMINO ACID DERIVATIVES AS COLLAGENASE INHIBITORS

[75] Inventors: Balraj K. Handa, Welwyn Garden City; William H. Johnson, Hitchin; Peter J. Machin, London, all of England

[73] Assignee: Hoffmann-La Roche Inc., Nutley, N.J.

[21] Appl. No.: 336,264

[22] Filed: Apr. 11, 1989

Related U.S. Application Data

[63] Continuation of Ser. No. 14,957, Feb. 17, 1987, abandoned.

[30] Foreign Application Priority Data

Mar. 11, 1986 [GB] United Kingdom ............... 8605977
Dec. 12, 1986 [GB] United Kingdom ............... 8629712

[51] Int. Cl.$^5$ ............... A61K 31/16; A61K 31/85; C07C 259/04; C07C 259/06
[52] U.S. Cl. ............... 562/621; 562/622; 562/623; 514/575
[58] Field of Search ............... 564/153; 260/500.5 H; 514/575; 562/621, 622, 623

[56] References Cited

U.S. PATENT DOCUMENTS

| | | | |
|---|---|---|---|
| 4,028,401 | 6/1977 | Fessler et al. ............... | 260/570.5 H |
| 4,599,361 | 7/1986 | Dickens et al. ............... | 260/570.5 H |
| 4,618,708 | 10/1985 | Roques et al. ............... | 562/448 |
| 4,671,901 | 6/1987 | Green ............... | 260/500.5 H X |
| 4,684,482 | 8/1987 | Green ............... | 260/500.5 H X |

FOREIGN PATENT DOCUMENTS

| | | | |
|---|---|---|---|
| 706911 | 3/1965 | Canada ............... | 260/500.5 H |
| 0038758 | 4/1980 | European Pat. Off. ............... | 514/575 |
| 0082088 | 12/1981 | European Pat. Off. ............... | 514/575 |
| 75896 | 1/1983 | European Pat. Off. ............... | 260/500.5 H |
| 126974 | 12/1984 | European Pat. Off. ............... | 260/500.5 H |
| 1133360 | 7/1962 | Fed. Rep. of Germany ... | 260/500.5 H |
| 1135890 | 9/1962 | Fed. Rep. of Germany ... | 260/500.5 H |
| 999582 | 7/1965 | United Kingdom ............... | 260/500.5 H |

OTHER PUBLICATIONS

Pipasquale et al., Proceedings Soc. Exptl. Biol. Med., vol. 183, pp. 262-267, (1986).
Nishino, N. et al., Pept. Procd. Am. Pept. Synp., 5th, 236-238, (1977).

Primary Examiner—Floyd D. Higel
Attorney, Agent, or Firm—George M. Gould; Bernard S. Leon; William G. Isgro

[57] ABSTRACT

Compounds of the formula

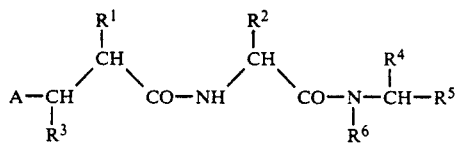

wherein A is a group of the formula HN(OH)—CO— or HCO—N(OH)—; $R^1$ is a $C_2$-$C_5$-alkyl; $R^2$ is the characterizing group of a natural α-amino acid in which any functional group present may be protected, any amino group present may be acylated and any carboxyl group present may be amidated, with the proviso that $R^2$ is not hydrogen or methyl; $R^3$ is hydrogen, amino, hydroxy, mercapto, $C_1$-$C_6$-alkyl, $C_1$-$C_4$-alkoxy, $C_1$-$C_6$-alkylamino, $C_1$-$C_6$-alkylthio or aryl-($C_1$-$C_6$-alkyl), or amino-($C_1$-$C_6$-alkyl), hydroxy-($C_1$-$C_6$-alkyl), mercapto-($C_1$-$C_6$-alkyl) or carboxy-($C_1$-$C_6$-alkyl) in which the amino, hydroxy, mercapto or carboxyl group may be protected, the amino group may be acylated or the carboxyl group may be amidated; $R^4$ is hydrogen or methyl; $R^5$ is hydrogen or a $C_1$-$C_6$-alkyl, $C_1$-$C_6$-alkoxy-$C_1$-$C_6$-alkyl, di($C_1$-$C_6$-alkoxy)-methylene, carboxyl, ($C_1$-$C_6$-alkyl)-carbonyl, ($C_1$-$C_6$-alkoxy)carbonyl, aryl-methoxycarbonyl, ($C_1$-$C_6$-alkyl)aminocarbonyl or arylaminocarbonyl; and $R^6$ is hydrogen or methyl; or $R^2$ and $R^4$ taken together are a group of the formula —$(CH_2)_n$— in which n is a number from 4 to 11; or $R^4$ and $R^6$ taken together are a trimethylene; and pharmaceutically acceptable salts of those compounds which are acidic or basic are described. The compounds of formula I possess collagenase inhibitory activity and can be used in the control or prevention of degenerative joint diseases.

36 Claims, No Drawings

HYDROXYLAMINE BEARING AMINO ACID DERIVATIVES AS COLLAGENASE INHIBITORS

This is a continuation, of application Ser. No. 07/014,957 filed Feb. 17, 1987, now abandoned.

BRIEF SUMMARY OF THE INVENTION

The hydroxylamine derivatives of the invention are compounds of the formula

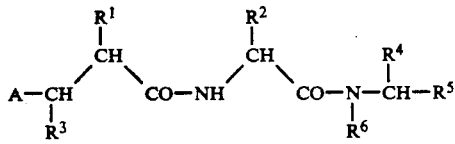

wherein
A is a group of the formula HN(OH)—CO— or HCO—N(OH)—;
$R^1$ is a $C_2$-$C_5$-alkyl;
$R^2$ is the characterizing group of a natural α-amino acid in which any functional group present may be protected, any amino group present may be acylated and any carboxyl group present may be amidated, with the proviso that $R^2$ is not hydrogen or methyl;
$R^3$ is hydrogen, amino, hydroxy, mercapto, $C_1$-$C_6$-alkyl, $C_1$-$C_6$-alkoxy $C_1$-$c_6$-alkylamino, $C_1$-$C_6$-alkylthio or aryl-($C_1$-$C_6$-alkyl), or amino-($C_1$-$C_6$-alkyl), hydroxy-($C_1$-$C_6$-alkyl). mercapto-($C_1$-$C_6$-alkyl) or carboxy-($C_1$-$C_6$-alkyl) in which the amino, hydroxy, mercapto or carboxyl group may be protected, the amino group may be acylated or the carboxyl group may be amidated;
$R^4$ is hydrogen or methyl;
$R^5$ is hydrogen, $C_1$-$C_6$-alkyl, $C_1$-$C_6$-alkoxy-$C_1$-$C_6$-alkyl, di($C_1$-$C_6$-alkoxy)-methylene, carboxyl, ($C_1$-$C_6$-alkyl)carbonyl, arylmethoxycarbonyl, ($C_1$-$C_6$-alkyl)aminocarbonyl or arylaminocarbonyl group; and
$R^6$ is hydrogen or methyl; or
$R^2$ and $R^4$ taken together are a group of the formula —$(CH_2)_n$— is which n stands for a number of 4 to 11; or
$R^4$ and $R^6$ taken together are trimethylene; and pharmaceutically acceptable salts of those compounds which are acidic or basic.

DETAILED DESCRIPTION OF THE INVENTION

The hydroxylamine derivatives of the invention are compounds of the formula

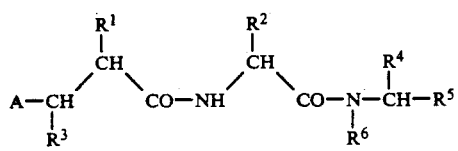

wherein
A is a group of the formula HN(OH)—CO— or HCO—N(OH)—;
$R^1$ is a $C_2$-$C_5$-alkyl;
$R^2$ is the characterizing group of a natural α-amino acid in which any functional group present may be protected, any amino group present may be acylated and any carboxyl group present may be amidated, with the proviso that $R^2$ is not hydrogen or methyl;
$R^3$ is hydrogen, amino, hydroxy, mercapto, $C_1$-$C_6$-alkyl, $C_1$-$C_6$-alkoxy, $C_1$-$C_6$-alkylamino, $C_1$-$C_6$-alkylthio or aryl-($C_1$-$C_6$-alkyl), or amino-($C_1$-$C_6$-alkyl), hydroxy-($C_1$-$C_6$-alkyl), mercapto-($C_1$-$C_6$-alkyl) or carboxy-($C_1$-$C_6$-alkyl) in which the amino, hydroxy, mercapto or carboxyl group may be protected, the amino group may be acylated or the carboxyl group may be amidated;
$R^4$ is hydrogen or methyl;
$R^5$ is hydrogen, $C_1$-$C_6$-alkyl, $C_1$-$C_6$-alkoxy-$C_1$-$C_6$-alkyl, di($C_1$-$C_6$-alkoxy)-methylene, carboxyl, ($C_1$-$C_6$-alkyl)carbonyl, ($C_1$-$C_6$-alkoxy)carbonyl, arylmethoxycarbonyl, ($C_1$-$C_6$-alkyl)aminocarbonyl or arylaminocarbonyl group; and
$R^6$ is hydrogen or methyl; or
$R^2$ and $R^4$ taken together are a group of the formula —$(CH_2)_n$— in which n stands for a number from 4 to 11; or
$R^4$ and $R^6$ taken together are trimethylene; and pharmaceutically acceptable salts of those compounds which are acidic or basic.

As used herein, the term "alkyl", alone or in combinations, denotes straight-chain and branched-chain saturated hydrocarbon groups containing the number of carbon atoms specified in the respective case, examples of alkyl groups are methyl, ethyl, n-propyl, isopropyl, n-butyl, sec. butyl, isobutyl, tert.butyl, n-pentyl and the like. The term "alkoxy" denotes alkyl ether groups in which the term "alkyl" has the above significance, examples of alkoxy groups are methoxy, ethoxy, n-propoxy, isopropoxy, n-butoxy, tert.butoxy and the like. The term "aryl" as used in connection with "aryl-($C_1$-$C_6$-alkyl)", "arylmethoxycarbonyl" and "arylaminocarbonyl" denotes a phenyl group which is optionally substituted with one or more substituents selected from $C_1$-$C_6$-alkyl, $C_1$-$C_6$-alkoxy, halogen, trifluromethyl and the like.

The term "characterizing group of a natural α-amino acid" denotes the group $R^2$ in an α-amino acid of the formula $H_2N$—$CH(R^2)$—COOH which is naturally occurring. Thus, having regard to the proviso with respect to $R^2$, the characterizing group can be one of the following, with the corresponding natural α-amino acid being indicated thereafter in parenthesis: isopropyl (valine), isobutyl (leucine), benzyl (phenylalanine), p-hydroxybenzyl (tyrosine), hydroxymethyl (serine), mercaptomethyl (cysteine), 1-hydroxyethyl (threonine), 2-methylthioethyl (methionine), carboxymethyl (aspartic acid), 2-carboxyethyl (glutamic acid), 3-guanidinopropyl (arginine), 4-aminobutyl (lysine) and the like.

Any functional group present in $R^2$ and any amino, hydroxy, mercapto or carboxyl group present in $R^3$ can be protected in a manner which is known in peptide chemistry. For example, a hydroxy group can be protected in the form of a readily cleavable ether such as the tert.butyl, benzyl or tetrahydropyranyl ether or in the form of a readily cleavable ester such as the acetate. A mercapto group can be protected, for example, by a tert.butyl, benzyl or like group. An amino group can be protected, for example, by a tert.butyoxycarbonyl, benzyloxycarbonyl, formyl, trityl, trifluoroacetyl. 2-(biphenylyl)-isopropoxycarbonyl or isobornyloxycarbonyl group or in the form of a phthalimido or like group.

A carboxy group can be protected, for example, in the form of a readily cleavable ester such as the methyl, ethyl, tert.butyl, benzyl or like ester.

An amino group present in $R^2$ and/or $R^3$ can be acylated with a non-cleavable acyl group, for example, an acyl group derived from an aromatic dicarboxylic acid or an aminocarboxylic acid. Examples of such aromatic dicarboxylic acids are benzenedicarboxylic acids such as phthalic acid, terephthalic acid and the like. Examples of such aminocarboxylic acids are α-amino acids such as the natural α-amino acids, for example, glycine, alanine and the like.

A carboxyl group present in $R^2$ and/or $R^3$ can be amidated in a conventional manner. Thus, examples of amidated carboxyl groups are the aminocarbonyl, ($C_1$–$C_6$-alkyl)aminocarbonyl, di($C_1$–$C_6$-alkyl)aminocarbonyl or arylaminocarbonyl groups as well as a carboxyl group amidated with an aminocarboxylic acid such as a natural α-amino acid, for example, glycine, alanine and the like.

The compounds of formula I, which are basic, form pharmaceutically acceptable salts with inorganic acids, for example, hydrohalic acids such as hydrochloric acid and hydrobromic acid, sulfuric acid, nitric acid, phosphoric acid and the like and with organic acids such as acetic acid, tartaric acid, succinic acid, fumaric acid, maleic acid, malic acid, salicylic acid, methanesulfonic acid, p-toluenesulfonic acid and the like. The compounds of formula I, which are acidic, form pharmaceutically acceptable salts with bases, for example, alkali metal hydroxides such as sodium hydroxide and potassium hydroxide, alkaline earth metal hydroxides such as calcium hydroxide and magnesium hydroxide, ammonium hydroxide and the like.

The compounds of formula I contain at least two asymmetric carbon atoms and can accordingly exist as optically active enantiomers, as diastereoisomers or as racemates.

In formula I above, $R^1$ preferably is $C_3$- or $C_4$-alkyl, especially n-propyl, isobutyl or sec.butyl. $R^2$ preferably is isopropyl or isobutyl, protected p-hydroxybenzyl, especially p-methoxybenzyl, or a protected or acylated 4-aminobutyl group, especially 4-tert.-butoxycarbonylamino-butyl, 4-glycylamino-butyl or 4-(4-carboxy-benzoylamino)-butyl. $R^3$ preferably is hydrogen, methyl or a protected 4-aminobutyl group, especially, hydrogen, methyl or a 4-phthaloylamino-butyl group. Preferably, $R^4$ is hydrogen or methyl or $R^2$ and $R^4$ taken together are a group of the formula —$(CH_2)_n$— in which n is a number from 5 to 9. When $R^4$ is hydrogen or methyl, $R^5$ preferably is hydrogen, $C_1$–$C_6$-alkyl, $C_1$–$C_6$-alkoxy-$C_1$–$C_6$-alkyl, di($C_1$–$c_6$-alkoxy)-methylene, carboxyl or ($C_1$–$C_6$-alkoxy)carbonyl, especially, carboxyl or ($C_1$–$C_6$-alkoxy)carbonyl, with the preferred ($C_1$–$C_6$-alkoxy)carbonyl group being ethoxycarbonyl. When $R^2$ and $R^4$ taken together are a group of the formula—$(CH_2)_n$—, $R^5$ preferably is hydrogen. $R^6$ preferably hydrogen.

Thus, it will be evident that especially preferred compounds of formula I provided by the invention are those in which $R^1$ is n-propyl, isobutyl or sec.butyl, $R^2$ is isopropyl, isobutyl, p-methoxy-benzyl 4-tert.butoxycarbonylamino-butyl, 4-glycylamino-butyl or 4-(4-carboxybenzoylamino)-butyl group, $R^3$ is hydrogen or methyl or 4-phthaloyl-amino-butyl, $R^4$ is hydrogen or methyl, $R^5$ is carboxyl or ethoxycarbonyl and $R^6$ is hydrogen or $R^2$ and $R^4$ taken together are a group of the formula—$(CH_2)_n$— in which n is a number from 5 to 9, $R^5$ is hydrogen and $R^6$ is hydrogen.

With respect to steroechemistry, the carbon atom to which $R^1$ is attached preferably has the (R)-configuration. The carbon atom to which $R^2$ is attached preferably has the (L)-configuration when $R^2$ is the side-chain of a natural α-amino acid, as hereinbefore defined. The carbon atom to which $R^3$ is attached has the (R)- or (S)-configuration depending on the nature of $R^3$. The preferred stereochemistry at this carbon atom has the groups in the same orientation as (S) when $R^3$ is $C_1$-$C_6$-alkyl. The carbon atom to which $R^4$ is attached preferably has the (S)-configuration when $R^4$ is methyl and $R^5$ is carboxyl, ($C_1$-$C_6$-alkoxy)carbonyl, arylmethoxycarbonyl, ($C_1$-$C_6$-alkyl)aminocarbonyl or arylcarbonylamino.

Particularly preferred hydroxylamine derivatives of formula I provided by the invention are:

[4-(N-Hydroxyamino) 2(R)-isobutylsuccinyl]-L-leucylglycine ethyl ester;

[4-(N-hydroxyamino) 2(R)-isobutylsuccinyl]-L-leucyl-L-alanine ethyl ester;

[N-formyl-N-hydroxy 2(RS)-isobutyl-3-aminopropionyl]-L-leucylglycine ether ester;

$N^α$-[4-(N-hydroxyamino) 2(R)-isobutylsuccinyl]-$N^{68}$-glycyl-L-lylsyl-L-alanine ethyl ester;

[4-(N-hydroxyamino) 2(R)-isocbutylsuccinyl]-3(RS)-aminolaurolactam and

[4-(N-hydroxyamino) 3(S)-phthaloylaminobutyl-2(R)-isobutylsuccinyl]-L-leucylglycine ethyl ester.

Examples of other interesting hydroxylamine derivatives of formula I provided by the invention are:

[4-(N-Hydroxyamino) 2(RS)-isobutylsuccinyl]-L-leucylglycine ethyl ester;

[4-(N-hydroxyamino) 2(RS)-isobutylsuccinyl]-L-leucylglycine isopentylamide;

[4-(N-hydroxyamino) 2(RS)-isobutylsuccinyl]-L-valylglycine ethylamide;

[4-(N-hydroxyamino) 2(RS)-isobutylsuccinyl]-L-leucylglycine ethylamide;

$N^α$-[4-(N-hydroxyamino) 2(RS)-isobutylsuccinyl]-$N^ε$-tert.butoxycarbonyl-L-lysylglycine ethylamide;

[4-(N-hydroxyamino) 2(RS)-isobutylsuccinyl]-O-methyl-L-tyrosinylglycine ethyl ester;

[4-(N-hydroxyamino) 2(RS)-isobutylsuccinyl]-O-methyl-L-tyrosinylglycine ethylamide;

[4-(N-hydroxyamino) 2(RS)-isobutylsuccinyl]-L-leucyl-L-alanine ethyl ester;

[4-(N-hydroxyamino) 2(RS)-isobutylsuccinyl]-L-leucine pentylamide;

[4-(N-hydroxyamino) 2(RS)-isobutylsuccinyl]-L-leucylglycine isopentyl ester;

[4-(N-hydroxyamino) 2(RS)-isobutylsuccinyl]-L-leucine methylamide;

[4-(N-hydroxyamino) 2(R)-propylsuccinyl]-L-leucylglycine ether ester;

[4-(N-hydroxyamino) 2(RS)-sec.butylsuccinyl]-L-leucylglycine ether ester;

[4-(N-hydroxyamino) 2(R)-isobutylsuccinyl]-L-leucyl-L-alanine;

[4-(N-hydroxyamino) 2(RS)-isobutylsuccinyl]-L-leucylglycine methyl ester;

[4-(N-hydroxyamino) 2(RS)-isobutylsuccinyl]-L-leucylsarcosine ethyl ester;

[4-(N-hydroxyamino) 2(RS)-isobutylsuccinyl]-L-leucyl-L-proline ether ester;

[4-(N-hydroxyamino) 2(RS)-isobutylsuccinyl]-L-leucyl-L-alanine isopropyl ester;

[4-(N-hydroxyamino) 2(RS)-isobutylsuccinyl]-L-leucine isopropylamide;

[4-(N-hydroxyamino) 2(RS)-isobutylsuccinyl]-L-leucine 2-oxopropylamide;

[4-(N-hydroxyamino) 2(RS)-isobutylsuccinyl]-L-leucine 2-methoxyethylamide;

[4-(N-hydroxyamino) 2(RS)-isobutylsuccinyl]-L-leucine 2,2-dimethoxyethylamide;

$N^\alpha$-[4-(N-hydroxyamino) 2(R)-isobutylsuccinyl]-$N^\epsilon$-glycyl-L-lysine methylamide;

$N^\alpha$-[4-(N-hydroxyamino) 2(R)-isobutylsuccinyl]-$N^\epsilon$-(4-carboxybenzoyl)-L-lysyl-L-alanine ethyl ester;

$N^\alpha$-[4-N-hydroxyamino) 2(R)-isobutylsuccinyl]-$N^\epsilon$-(4-carboxybenzoyl)-L-lysyl-L-alanine;

[4-(N-hydroxyamino) 2(R)-isobutylsuccinyl]-3(RS)-amino-octahydro-2H-azonin-2-one;

[4-(N-hydroxyamino) 3(S)-methyl-2(R)-isobutylsuccinyl]-L-leucylglycine ether ester;

[N-formyl-N-hydroxy 2(RS)-isobutyl-3-aminopropionyl]-L-leucyl-L-alanine ethyl ester;

[N-formyl-N-hydroxy 2(RS))-isobutyl-3-aminopropionyl]-L-leucine methylamide, and the like.

The compounds provided by the invention, as well as pharmaceutically acceptable salts of those compounds which are acidic or basic, can be prepared by hydrogenolyzing of hydrolyzing a compound of the formula

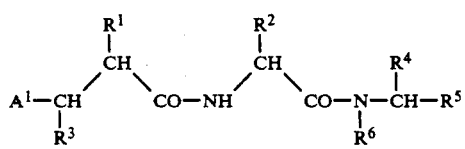

wherein $A^1$ is a group of the formula $HN(R^7)$—CO— or HCO—$N(R^7)$— in which $R^7$ is a group convertible into a hydroxy group by hydrogenolysis or hydrolysis and $R^1$, $R^2$, $R^3$, $R^4$, $R^5$ and $R^6$ have the significance given earlier.

and, if desired, converting an acidic or basic product obtained into a pharmaceutically acceptable salt.

The symbol $R^7$ in formula II above can be any group which can be converted into a hydroxy group by hydrolysis or hydrogenolysis. Examples of such groups are the benzyloxy, tetrahydropyranyloxy, benzhydryloxy, trityloxy and tert.butoxy.

The conversion of the group denoted by $R^7$ into a hydroxy group by hydrogenolysis can be carried out in a manner known using a hydrogenation catalyst which is conventionally used for this purpose, for example, a palladium catalyst. The hydrogenolysis is carried out under generally known conditions, for example, in an inert organic solvent, for example, alkanol such as methanol, ethanol and the like, dimethylformamide and the like and at room temperature and under atmospheric pressure. In a preferred embodiment $R^7$ is benzyloxy.

The conversion of the group denoted by $R^7$ into a hydroxy group by hydrolysis can also be carried out in a manner known by treatment with an organic or inorganic acid. Examples of acids which can be used are alkanecarboxylic acids such as acetic acid and the like, trifluoroacetic acid, aromatic sulfonic acids such as p-toluenesulfonic acid and mineral acids such as sulfuric acid and hydrohalic acids, for example, hydrochloric acid or hydrobromic acid. The hydrolysis is carried out in a conventional manner; for example, in an aqueous medium or in an organic solvent and at room temperature and under atmospheric pressure. When the hydrolysis is carried out using an organic acid, the acid can itself serve as the solvent. In a preferred embodiment, $R^7$ is tetrahydropyranyl and, in this case, the hydrolysis is conveniently carried out in an aqueous medium.

The conversion of a resulting compound of formula I which is acidic or basic into a pharmaceutically acceptable salt can be carried out in a known manner by treatment with an appropriate base or acid, respectively.

The compounds of formula II which are used as starting materials in the process provided by the invention also form part of the invention.

The compounds of formula II in which $A^1$ is a group of the formula $HN(R^7)$—CO— can be prepared, for example, by condensing a compound of the formula

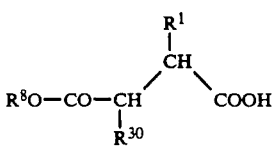

wherein $R^1$ has the significance given earlier, $R^8$ is a protecting group and $R^{30}$ has the same significance as $R^3$ with the proviso that any amino, hydroxy, mercapto or carboxyl group present is protected, with a compound of the formula

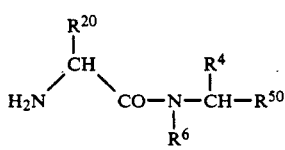

wherein $R^4$ and $R^6$ have the significance given earlier, $R^{20}$ has the same significance as $R^2$ with the proviso that any functional group present is protected and $R^{50}$ has the same significance as $R^5$ except that any carboxyl group is protected. cleaving the protecting group denoted by $R^8$ from the resulting compound of the formula

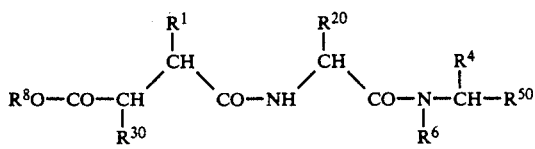

wherein $R^1$, $R^4$ $R^6$, $R^8$, $R^{20}$, $R^{30}$ and $R^{50}$ have the significance given earlier. condensing the resulting compound of the formula

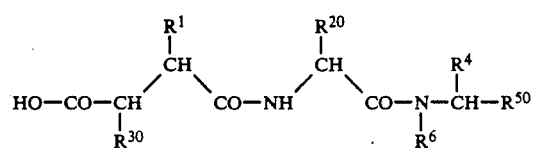

wherein $R^1$, $R^4$, $R^6$, $R^{20}$, $R^{30}$ and $R^{50}$ have the significance given earlier, with a compound of the formula $R^7$—$NH_2$      VII wherein $R^7$ has the significance given earlier, and, if desired, and in either sequence, cleaving any protecting groups present in R$^{20}$ and/or R$^{30}$ and converting any protected carboxyl group denoted by R$^{50}$ into a carboxyl group.

In the above procedure for the preparation of the compounds of formula II in which A$^1$ is a group of the formula HN(R$^7$)—CO—, it will be appreciated that, in the compounds of formulas IV and III, any protecting group present in R$^{20}$ and R$^{30}$, respectively, as well as the protecting group in R$^{50}$ must be of a kind which is not cleaved under the same conditions as the protecting group denoted by R$^8$.

The symbol R$^8$ in formula III can be any conventional carboxyl protecting group; for example, the methyl, ethyl, tert.butyl, benzyl or the like.

The condensation of a compound of formula III with a compound of formula IV can be carried out in a manner which is known in peptide chemistry. Thus, for example, the condensation can be carried out according to the acid halide, acid azide, acid anhydride, activated amide, mixed carbonic anhydride or activated ester method.

The cleavage of the protecting group denoted by R$^8$ from a compound of formula V can be carried out in a known manner; for example by hydrolysis as described earlier.

The condensation of a compound of formula VI with a compound of formula VII can be carried out in a conventional manner; for example, as described earlier in connection with the condensation of a compound of formula III with a compound of formula IV.

Any protecting groups present in R$^{20}$ and/or R$^{30}$ in the condensation product can be cleaved, if desired, according to known methods in peptide chemistry. Further, where R$^{50}$ is a protected carboxyl group, this can be converted, if desired, into a carboxyl group in a known manner; for example, by saponification, treatment with anhydrous trifluoroacetic acid, hydrogenolysis or the like, depending on the nature of the protecting group.

Another procedure, for the preparation of the compounds of formula II in which A$^1$ is a group of the formula HN(R$^7$)—CO— and R$^2$ is the characterizing group of a natural α-amino acid as defined earlier, comprises condensing a compound of formula III given earlier with a compound of the formula

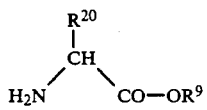

wherein R$^{20}$ has the same significance as R$^2$ with the proviso that any functional group present is protected and R$^9$ is a carboxyl protecting group, cleaving the protecting group denoted by R$^8$ in the resulting compound of the formula

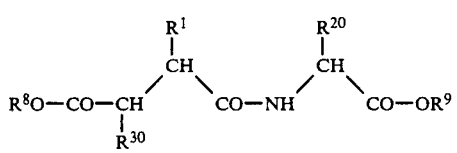

wherein R$^1$, R$^8$, R$^9$, R$^{20}$ and R$^{30}$ have the significance given earlier, condensing the thus-obtained compound of the formula

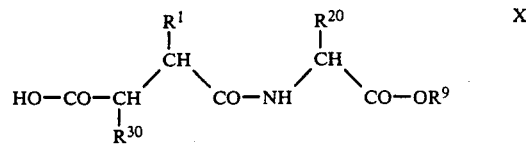

wherein R$^1$, R$^9$, R$^{20}$ and R$^{30}$ have the significance given earlier, with a compound of formula VII given earlier, cleaving the protecting group denoted by R$^9$ in the resulting compound of the formula

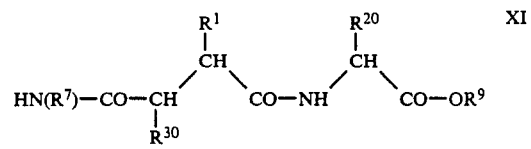

wherein R$^1$, R$^7$, R$^9$, R$^{20}$ and R$^{30}$ have the significance given earlier, condensing the thus-obtained compound of the formula

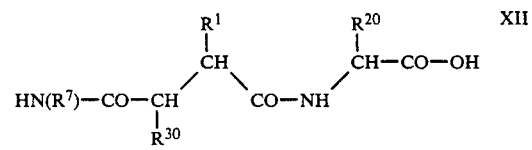

wherein R$^1$, R$^7$, R$^{20}$ and R$^{30}$ have the significance given earlier, with a compound of the formula

wherein R$^4$, R$^6$ and R$^{50}$ have the significance given earlier, and, if desired and in either sequence, cleaving any protecting groups present in R$^{20}$ and/or R$^{30}$ and converting any protected carboxyl group denoted by R$^{50}$ into a carboxyl group.

In the above-described procedure, it will again be appreciated that in the compounds of formulas VIII and III any protecting group present in R$^{20}$ and R$^{30}$, respectively, as well as the protecting group denoted by R$^9$ must be of a kind which is not cleaved under the same conditions as the group denoted by R$^8$.

The condensation of a compound of formula III with a compound of formula VIII can be carried out in the same manner to that described earlier in connection with the condensation of a compound of formula III with a compound of formula IV.

The cleavage of the group denoted by R$^8$ from a compound of formula IX can be carried out in same manner to that described earlier in connection with the cleavage of the group denoted by R$^8$ from a compound of formula V.

The condensation of a compound of formula X with a compound of formula VII can be carried out in the same manner to that described earlier in connection with the condensation of a compound of formula III with a compound of formula IV.

The cleavage of the protecting group denoted by R$^9$ from a compound of formula XI can be carried out in a known manner; for example, by saponification, treatment with anhydrous trifluoroacetic acid, hydrogenolysis and the like, depending on the nature of the protecting group.

The condensation of a compound of formula XII with a compound of formula XIII can be carried out in the same manner to that described earlier in connection with the condensation of a compound of formula III with a compound of formula IV.

The subsequent optional cleavage of any protecting group present in $R^{20}$ and/or $R^{30}$ and conversion of any protected carboxyl group denoted by $R^{50}$ into a carboxyl group can be carried out as described earlier.

The compounds of formula II in which $A^1$ is a group of the formula HCO—N($R^7$)— can be prepared, for example, by condensing a compound of the formula

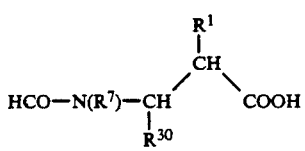

XIV wherein $R^1$, $R^7$ and $R^{30}$ have the significance given earlier, with a compound of formula IV given earlier and, if desired and in either sequence, cleaving any protecting groups present in $R^{20}$ and/or $R^{30}$ and converting any protected carboxy group denoted by $R^{50}$ in a carboxyl group.

The condensation of a compound of formula XIV with a compound of formula IV can be carried out in the same manner to that described earlier in connection with the condensation of a compound of formula III with a compound of formula IV.

The subsequent optional cleavage of any protecting group present in $R^{20}$ and/or $R^{30}$ and the conversion of any protected carboxy group denoted by $R^{50}$ into a carboxyl group can be carried out as described earlier.

The compounds of formulas III, IV, VII, VIII, XIII and XIV hereinbefore, insofar as they are not known compounds or analogues of known compounds, can be obtained as described in the following Examples or in analogy thereto.

The hydroxylamine derivatives provided by the invention possess collagenase inhibitory activity and can be used in the treatment of degenerative joint diseases such as rheumatoid arthritis and osteoarthritis.

The in vitro inhibitory activity of the hydroxylamine derivatives of formula I against collagenase obtained from a culture of human synovial fibroblasts according to the method of Dayer J-M et al., Proc. Natl. Acad. Sci. USA (1976), 73, 945 can be demonstrated using the following test procedure:

Procollagenase was partially purified from the cell culture medium by negative adsorption on DEAE Sephadex A-50 at pH 8.1 and activated by treatment with tryspin. The inhibitory activity of the present hydroxylamine derivatives was determined using a synthetic substrate, N-acetyl-L-prolyl-L-leucylglycyl-L-leucyl-L-leucylglycyl ether ester, for this collagenase. The enzyme was added to a solution of 0.5 mmol of substrate in 50 mmol of borate buffer (pH 7.5) containing 1 mmol of calcium chloride and a known concentration of peptide derivative. The resulting solution was incubated at 37° C. for 1 hour. Enzyme digestion of the substrate was terminated by the addition of an equal volume of 2% (weight/volume) sodium hydrogen carbonate solution in 50% aqueous methanol containing 0.1% (weight/volume) of picrylsulfonic acid. The solution obtained was incubated at 37° C. for an additional 1 hour in order to allow reaction between the L-leucyl-L-leucyl-glycyl ethyl ester generated by the cleavage of the substrate and the picrylsulfonic acid to give trinitrophenyl-L-leucyl-L-leucylglycyl ethyl ester. The reaction was terminated and stabilized by acidification with IN hydrochloric acid. The concentration of trinitrophenyl-L-leucyl-L-leucylglycyl ethyl ester was determined by spectrophotometry at 335 nm. The $IC_{50}$ is that concentration of hydroxylamine derivative of formula I of the invention in the enzyme digestion which reduces substrate cleavage to 50% of that achieved by the enzyme alone.

The results obtained in the foregoing test with representative hydroxylamine derivatives of formula I provided by the invention are compiled in the following Table:

TABLE

| Hydroxylamine derivative | Inhibitory activity against human synovial collagenase $IC_{50}$ (mol) |
|---|---|
| A | $2.5 \times 10^{-8}$ |
| B | $8.5 \times 10^{-9}$ |
| C | $3.0 \times 10^{-7}$ |
| D | $3.0 \times 10^{-8}$ |
| E | $3.8 \times 10^{-8}$ |
| F | $1.2 \times 10^{-8}$ |

A: [4-(N-Hydroxyamino) 2(R)-isobutylsuccinyl]-L-leucyl-glycine ethyl ester;
B: [4-(N-hydroxyamino) 2(R)-isobutylsuccinyl]-L-leucyl-L-alanine ethyl ester;
C: [N-formyl-N-hydroxy 2(RS)-isobutyl-3-aminopropionyl]-L-leucylglycine ethyl ester;
D: $N^\alpha$-[4-(N-hydroxyamino) 2(R)-isobutylsuccinyl]-$N^\epsilon$-glycyl-L-lysyl-L-alanine ethyl ester;
E: [4-(N-hydroxyamino) 2(R)-isobutylsuccinyl]-3(RS)-aminolaurolactam;
F: [4-(N-hydroxyamino) 3(S)-phthaloylaminobutyl-2(R)-iso-butylsuccinyl]-L-leucylglycine ethyl ester.

The hydroxylamine derivatives of formula I provided by the invention can be used as medicaments in the form of pharmaceutical preparations which contain them in association with a compatible pharmaceutical carrier material. This carrier material can be an organic or inorganic carrier material which is suitable for enteral or parenteral administration such as water, lactose, starch, magnesium stearate, talc, gum arabic, gelatine, polyalkylene glycols, petroleum jelly and the like. The pharmaceutical preparations can be made up in a solid form, for example, as tablets, powders, dragees, suppositories, capsules and the like, or in a liquid form, for example, as solutions, emulsions, suspensions and the like.

If necessary, the pharmaceutical preparations can be subjected to conventional pharmaceutical operations such as sterilization and the like and they can also contain conventional pharmaceutical adjuvants such as preserving agents, stabilizing agents, wetting agents, salts for varying the osmotic pressure and the like. The present pharmaceutical preparations may also contain other therapeutically valuable substances.

The pharmaceutical preparations can be prepared by mixing a hydroxylamine derivative of formula I provided by the invention with a compatible pharmaceutical carrier material and bringing the mixture obtained into the desired pharmaceutical dosage form.

The hydroxylamine derivatives provided by the invention may be administered to adults in a dosage range of from about 5 mg to 30 mg, preferably about 10 mg to 15 mg, per day. It will, of course be appreciated that this dosage range is given by way of example only and that it can be varied upwards or downwards depending on factors such as the potency of the particular compound to be administered, the particular condition to be treated and the individual requirements of the patient.

The Examples which follow further illustrate the invention. The structure of the products was confirmed by NMR spectroscopy and mass spectroscopy. The composition of thin-layer chromatography systems was as follows:

System A: chloroform: methanol: acetic acid: water 120:15:3:2.

System B: chloroform: methanol: acetic acid: water 60:18:2:3.

System C: chloroform: methanol: acetic acid: water 240:24:3:2.

EXAMPLE 1

0.5 g of [4-(N-benzyloxyamino) 2(RS)-isobutylsuccinyl]-L-leucylglycine ether ester in 10 ml of ethanol was hydrogenated for 1 hour in the presence of 0.1 g of 5% palladium/carbon. The mixture was filtered, the filtrate was evaporated and the residue was dried in vacuo to yield 0.38 g (96%) of [4-(N-hydroxyamino) 2(RS)-isobutylsuccinyl]-L-leucylglycine ethyl ester as a foam.

The [4-(N-benzyloxyamino) 2(RS)-isobutylsuccinyl]-L-leucylglycine ethyl ester used as the starting material was prepared as follows:

(A) 49.4 g of potassium tert.butoxide in 350 ml of tert.butanol were stirred and heated under reflux under nitrogen. A mixture of 36.4 ml of isobutyraldehyde and 83.2 ml of diethyl succinate was added over a period of 0.25 hour and the mixture was heated under reflux for 1.5 hours. The solution was evaporated to a small volume, acidified with 2N hydrochloric acid and the evaporation was continued. The residue, diluted with water, was extracted three times with 300 ml of diethyl ether each time and the ether solutions were combined, washed with water and extracted three times with 200 ml of 10% potassium carbonate solution each time. The basic solution was acidified with concentrated hydrochloric acid and the product was extracted into diethyl ether, washed with water, dried over anhydrous magnesium sulfate and evaporated to give an oil. This oil was dissolved in 400 ml of ethanol and the solution was hydrogenated for 2 hours in the presence of 5 g of 5% palladium/carbon. After filtration and evaporation of the filtrate there were obtained 69.8 g of crude 1-ethyl hydrogen 2(RS)-isobutylsuccinate.

(B) The foregoing ethyl ester in 800 ml of dichloromethane, 800 ml of isobutene and 8 ml of sulfuric acid was stirred in a sealed flask for 5 days. 350 ml of 5% sodium hydrogen carbonate solution were added and the solution was evaporated. The product was extracted from the aqueous residue with two 300 ml portions of diethyl ether. The ethereal extracts were washed with water and saturated sodium chloride solution, dried over anhydrous magnesium sulfate and evaporated to give 87.3 g of 4-tert.butyl 1-ethyl 2(RS)-isobutylsuccinate.

(C) The diester prepared in paragraph (B) in 500 ml of ethanol, 380 ml of water and 120 ml of 4N sodium hydroxide solution was stirred at room temperature for 16 hours. The ethanol was removed by evaporation, the solution was diluted with 300 ml of water, extracted twice with 400 ml of diethyl ether each time and acidified with concentrated hydrochloric acid. The product was taken up in diethyl ether, washed with water and saturated sodium chloride solution, dried over anhydrous magnesium sulfate and evaporated to give an oil. Chromatography on silica gel using toluene/acetic acid (19:1) for the elution followed by evaporation and removal of traces of acetic acid by evaporation with toluene yielded 45.5 g (49%) of 4-tert.butyl hydrogen 2(RS)-isobutylsuccinate as an oil, Rf (toluene/acetic acid 19:1) 0.32.

(D) 3.85 g of N-benzyloxycarbonyl-L-leucyl-glycine ethyl ester wee treated for 1 hour with 10 ml of 4N hydrogen bromide in acetic acid. 200 ml of diethyl ethyl were added and the precipitated gum was washed by two-fold decantation with 100 ml of diethyl ether each time, dried in vacuo and dissolved in 50 ml of tetrahydrofuran. The solution was cooled to 0° C. and neutralized with 3.0 ml of N-ethylmorpholine. 2.3 g of 4-tert.butyl hydrogen 2(RS)-isobutylsuccinate, 1.49 g of hydroxybenzotriazole and 2.26 g of N,N'-di-cyclohexylcarbodiimide were added and the mixture was stirred at 0° C. for 1 hour and then left to stand at 0° C. overnight. The solution was filtered and the filtrate was evaporated. The residue was taken up in ethyl acetate, washed in sequence with water 5% citric acid solution, water, 5% sodium hydrogen carbonate solution and saturated sodium chloride solution, dried over anhydrous magnesium sulfate and evaporated to give an oil. Chromatography on silica gel using for the elution ethyl acetate/hexane (a gradient from 1:9 to 1:1) yielded 2.54 g (59%) of [4-tert.butyl 2(RS)-isobutylsuccinyl]-L-leucylglycine ethyl ester as an oil, Rf (ethyl acetate/hexane 1:1) 0.73, 0.79.

(E) 2.54 g of [4-tert.butyl 2(RS)-isobutylsuccinyl]-L-leucylglycine ethyl ester were treated for 0.25 hour with 5 ml of 4N hydrogen bromide in acetic acid. The solution was evaporated and the resulting oil was dissolved in ethyl acetate, washed with water and saturated sodium chloride solution, dried over anhydrous magnesium sulfate and evaporated to give 2.1 g (96%) of an oil. This oil was taken up in 30 ml of tetrahydrofuran, the solution was cooled to −12° C., 0.72 ml of N-ethylmorpholine and 0.74 ml of isobutyl chloroformate were added and the mixture was stirred at −12° C. for 4 minutes. A solution of O-benzylhydroxylamine (prepared from 0.9 g of O-benzylhydroxylamine hydrochloride and 0.72 ml of N-ethylmorpholine in 5 ml of dimethylformamide at 0° C.) was added, the mixture was stirred at 0° C. for 1 hour and then left to stand at room temperature overnight. The solvent was removed by evaporation and the residue was dissolved in ethyl acetate. The solution was washed in sequence with water, 5% citric acid solution, water, 5% sodium hydrogen carbonate solution and saturated sodium chloride solution, dried over anhydrous magnesium sulfate and evaporated to give an oil. Chromatography on 75 g of silica gel using chloroform for the elution yielded 1.73 g (64%) of [4-(N-benzyloxyamino) 2(RS)-isobutylsuccinyl]-L-leucyl-glycine ethyl ester as an oil.

EXAMPLE 2

0.28 of [4-(N-benzyloxyamino) 2(RS)-isobutylsuccinyl-L-leucylglycine ethyl ester was separated into two isomers by HPLC on a Partesil (10 micron) ODS-3 column using acetonitrile/water (1:1) for the elution at a flow rate of 1.4 ml/minute. The first isomer (R₅=2.5 minutes) (0.13 g) in 5 ml of ethanol was hydrogenated for 1 hour in the presence of 20 mg of 5% palladium/carbon. The mixture was filtered, the filtrate was evaporated and the residue was dried in vacuo to yield 0.087 g (81%) of [4-(N-hydroxyamino) 2(R)-isobutyl-succinyl]-L-leucylglycine ethyl ester as a foam.

EXAMPLE 3

0.2 g of [4-(N-benzyloxyamino) 2(RS)-isobutylsuccinyl]-L-leucylglycine isopentylamide in 5 ml of ethanol was hydrogenated for 1 hour in the presence of 50 mg of 5% palladium/carbon. The mixture was filtered, the filtrate was evaporated and the residue was dried in vacuo to yield 0.102 g (61%) of [4-(N-hydroxyamino) 2(RS)-isobutylsuccinyl]-L-leucylglycine isopentylamide.

The [4-(N-benzyloxyamino) 2(RS)-isobutylsuccinyl]-L-leucylglycine isopentylamide used as the starting material was prepared as follows:

(A) 1.79 g of N-benzyloxycarbonyl-L-leucyl-glycine isopentylamide were treated with 5 ml of 4N hydrogen bromide/acetic acid for 1 hour. 150 ml of diethyl ether were added and the resulting L-leucylglycine isopentylamide hydrobromide was filtered and dried in vacuo.

1.05 g of 4-tert.butyl hydrogen 2(RS)-isobutylsuccinate in 10 ml of tetrahydrofuran were treated at $-21°$ C. with 0.58 ml of N-ethylmorpholine and 0.60 ml of isobutyl chloroformate and the mixture was stirred at $-12°$ C. for 4 minutes. A solution of the above hydrobromide salt in 5 ml of dimethylformamide was cooled to 0° C. and neutralized with 0.9 ml of N-ethylmorpholine. The two solutions were mixed and the mixture was stirred at 0° C. for 4 hours. The solvent was removed by evaporation and the residue was dissolved in ethyl acetate. The solution was washed in sequence with 5% citric acid solution, water, 5% sodium hydrogen carbonate solution and saturated sodium chloride solution, dried over anhydrous magnesium sulfate and evaporated to give 2.04 g (95%) of [4-tert.butyl 2(RS)-isobutylsuccinyl]-L-leucylglycine isopentylamide as a foam. Rf (methanol/chloroform 1:19) 0.59.

(B) 2.0 g of [4-tert.butyl 2(RS)-isobutyl-succinyl]-L-leucylglycine isopentylamide were taken up in 2 ml of ethyl acetate and treated with 5 ml of 4N hydrogen bromide in acetic acid for 2 hours. The mixture was evaporated to dryness and the residue was evaporated with toluene in order to remove traces of acetic acid. The residue was taken up in dichloromethane and extracted three times with 5% sodium hydrogen carbonate solution. The aqueous solutions were combined and acidified with 2N hydrochloric acid. Extraction with dichloromethane, washing with saturated sodium chloride solution and evaporation yielded 1.2 g of 2(RS)-isobutylsuccinyl-L-leucylglycine isopentylamide as a foam. The acid was taken up in 10 ml of tetrahydrofuran, the solution was cooled to $-12°$ C., 0.37 ml of N-ethylmorpholine and 0.38 ml of isobutyl choroformate were added and the resulting solution was stirred at $-12°$ C. for 4 minutes. 0.36 g of O-benzylhydroxylamine in 2 ml of tetrahydrofuran was added and the mixture was stirred at 0° C. for 2 hours. The solvent was removed by evaporation and the residue was dissolved in ethyl acetate. The solution was washed in sequence with 5% citric acid solution, water, 5% sodium hydrogen carbonate solution and saturated sodium chloride solution, dried over anhydrous magnesium sulphate and evaporated to give an oil. Chromatography on 50 g of silica gel using 3% methanol in chloroform for the elution yielded 0.92 g (61%) of [4-(N-benzyloxyamino) 2(RS)-isobutylsuccinyl]-L-leucylglycine isopentylamide as a foam.

EXAMPLE 4

In a manner analogous to that described in the first paragraph of Example 3, from [4-(N-benzyloxyamino) 2(RS)-isobutylsuccinyl]-L-valylglycine ethylamide there was obtained [4-(N-hydroxyamino) 2(RS)-isobutylsuccinyl]-L-valylglycine ethylamide in a yield of 83%.

The [4-(N-benzyloxyamino) 2(RS)-isobutylsuccinyl]-L-valylglycine ethylamide used as the starting material was prepared as follows:

(A) In a manner analogous to that described in Example 3(A), from N-benzyloxycarbonyl-L-valylglycine ethylamide there was obtained [4-tert.butyl 2(RS)-isobutylsuccinyl]-L-valylglycine ethylamide in a yield of 92%. Rf (methanol/chloroform 1:9) 0.62.

In a manner analogous to that described in Example 3(B), from [4-tert.butyl 2(RS)-isobutylsuccinyl]-L-valylglycine ethylamide there was obtained [4-(N-benzyloxyamino) 2(RS)-isobutylsuccinyl]-L-valylglycine ethylamide in a yield of 42%.

EXAMPLE 5

0.2 g of [4-(N-benzyloxyamino) 2(RS)-isobutylsuccinyl]-L-leucylglycine ethylamide in 5 ml of ethanol was hydrogenated for 1hour in the presence of 50 mg of 5% palladium/carbon. The mixture was filtered, the filtrate was evaporated and the residue was dried in vacuo to yield 0.16 g (99%) of [4-hydroxyamino) 2(RS)-isobutylsuccinyl]-L-leucylglycine ethylamide as a foam.

The [4-N-benzyloxyamino) 2(RS)-isobutylsuccinyl]-L-leucylglycine ethylamide used as the starting material was prepared in a manner analogous to that described in Example 3(A) and (B).

EXAMPLE 6

2.56 g of $N^\alpha$-[4-tert.butyl 2(RS)-isobutylsuccinyl]-$N^\epsilon$-tert. butyloxycarbonyl-L-lysylglycine ethylamide were treated with 4N hydrogen chloride in ethyl acetate for 3 hours. The solvent was removed by evaporation, toluene was added and the mixture was then evaporated to yield a foam. This foam was taken up in 20 ml of dioxane and 20 ml 2N sodium hydroxide solution and the mixture was treated at 0° C. with 4.3 g of di-tert.butyl dicarbonate for 16 hours. The dioxane was removed by evaporation, the solution was diluted with 20 ml of water, extracted with ethyl acetate and acidified to pH 3 with 2N hydrochloric acid. The product was taken up to ethyl acetate, washed with water and saturated sodium chloride solution, dried over magnesium sulfate and evaporated to give $N^\alpha$-[2-(RS)-isobutylsuccinyl]-$N^\epsilon$-tert.butyl-oxycarbonyl-L-lysylglycine ethylamide in the form of an oil. The acid was coupled to O-benzylhydroxylamine according to the procedure described in Example 3(B) to yield 1.04 g (37%) of $N^\alpha$-[4-(N-benzyloxyamino) 2(RS)-isobutylsuccinyl]-$N^\epsilon$-tert. butyloxycarbonyl-L-lysyl-glycine ethylamide: Rf (chloroform/methanol 9:1) 0.46. The benzyl protecting group was removed as described in the first paragraph of Example 3 to yield $N^\alpha$-[4-(N-hydroxyamino) 2(RS)-isobutylsuccinyl]-$N^\epsilon$-tert.butoxy-carbonyl-L-lysylglycine ethylamide in 86% yield as a foam.

EXAMPLE 7

In a manner analogous to that described in Example 3, there was prepared [4-(N-hydroxyamino) 2(RS)-isobutylsuccinyl]-O-methyl-L-tyrosinylglycine ethyl ester as a solid. Rd (chloroform/methanol 9:1) 0.23.

EXAMPLE 8

In a manner analogous to that described in Example 3, there was prepared [4-(N-hydroxyamino) 2(RS)-isobutylsuccinyl]-O-methyl-L-tyrosinylglycine ethylamide as a foam. Rf (chloroform/methanol 9:1) 0.46.

EXAMPLE 9

In a manner analogous to that described in Example 3, there was prepared [4-(N-hydroxyamino) 2(RS)-isobutylsuccinyl]-L-leucyl-L-alanine ethyl ester as a foam. Rf (chloroform/methanol 9:1) 0.60 and 0.65.

EXAMPLE 10

In a manner analogous to that described in Example 3, there was prepared [4-(N-hydroxyamino) 2(RS)-isobutylsuccinyl]-L-leucine pentylamide. RF (System A) 0.56.

EXAMPLE 11

In a manner analogous to that described in Example 3, there was prepared [4-(N-hydroxyamino) 2(RS)-isobutylsuccinyl]-L-leucylglycine isopentyl ester. Rf (ethyl acetate) 0.46.

EXAMPLE 12

In a manner analogous to that described in Example 3, there was prepared [4-(N-hydroxyamino) 2(RS)-isobutylsuccinyl]-L-leucine methylamide. Rf (System A) 0.45.

EXAMPLE 13

6.4 g of [4-(N-benzyloxyamino) 2(R)-isobutylsuccinyl]-L-leucyl-L-alanine ethyl ester were dissolved in 200 ml of ethanol and hydrogenated in the presence of 1 g of 5% palladium/carbon at room temperature and under atmospheric pressure. After 1.5 hours, the catalyst was removed by filtration and the solvent was removed by evaporation to yield 5.0 g (95%) of [4-(N-hydroxyamino) 2(R)-isobutylsuccinyl]-L-leucyl-L-alanine ethyl ester as a solid of melting point 175°–177° C.

The [4-(N-benzyloxyamino) 2(R)-isobutylsuccinyl]-L-leucyl-L-alanine ethyl ester used as the starting material was prepared as follows:

(A) 10.45 g of D-leucic acid was dissolved in 150 ml of ethyl acetate. 11 ml of triethylamine and 18.78 g of 4-nitrobenzyl bromide were added and the mixture was heated under reflux for 3 hours. The mixture was washed in sequence with water, 10% citric acid solution, saturated sodium hydrogen carbonate solution, water and saturated sodium chloride solution. After drying over anhydrous sodium sulfate and evaporation, there were obtained 20.6 g (98%) of D-leucic acid 4-nitrobenzyl ester as a gum. Rf (chloroform) 0.37.

(b) A solution of 20.6 g of D-leucic acid 4-nitrobenzyl ester and 6.1 g of pyridine in 100 ml of dry dichloromethane was added while stirring over a period of 10 minutes, to a solution of 21.72 g of trifluoromethanesulphonic anhydride in 180 ml of dry dichloromethane at 0° C. The mixture was stirred at 0° C. for an additional 0.5 hour. The solution was washed with water and saturated sodium chloride solution and dried over anhydrous sodium sulfate. After filtration, the filtrate was added dropwise at 0° C. to a suspension of 2.3 g of 80% sodium hydride and 16.63 g of di-tert.butyl malonate in 140 ml of dry dimethylformamide. The mixture was stirred at room temperature for 3 hours. The solvent was removed by evaporation and the oily residue was partitioned between ethyl acetate and water. The aqueous phase was extracted three times with 50 ml of ethyl acetate each time. The combined ethyl acetate extracts were washed with water and saturated sodium chloride solution, dried over anhydrous sodium sulfate and evaporated to give 34 g of 1-(4-nitrobenzyl) 4-tert.butyl 3-tert.butoxycarbonyl 2(R)-isobutylsuccinate as an oil in 95% yield. Rf (hexane/diethyl ether 1:1) 0.38.

(C) 30 g of 1-(4-nitrobenzyl) 4-tert.butyl 3-tert.butoxycarbonyl 2(R)-isobutylsuccinate were dissolved in 100 ml of trifluoroacetic acid and the solution was stirred at room temperature for 1 hour. The solvent was removed by evaporation and the resulting gum was treated several times with dry toluene and evaporated each time. It was then dissolved in 100 ml of dry toluene and the solution was heated at 110° C. for 2 hours. The solvent was removed by evaporation to give 18 g (90%) of 1-(4-nitrobenzyl) hydrogen 2(R)-isobutylsuccinate as a pale yellow oil. Rf (System A) 0.38.

(D) 9.4 g of 1-(4-nitrobenzyl) hydrogen 2(R)-isobutylsuccinate were dissolved in 30 ml of dry diethyl ether and the solution was cooled in a dry-ice/acetone bath. There were then added 70 ml of isobutene, followed dropwise by 0.64 ml of concentrated sulfuric acid. The reaction flask was tightly topped and the mixture was stirred at room temperature for 2 days. The mixture was made basic with saturated sodium hydrogen carbonate solution and water was added. The organic phase was separated and the aqueous phase was extracted twice more with diethyl ether. The combined ethereal phases were washed with water and saturated sodium chloride solution, dried over anhydrous sodium sulfate and evaporated to give 8.8 g (77%) of 4-tert.butyl 1-(4nitrobenzyl) 2(R)-isobutylsuccinate in the form of an oil. Rf (System A) 0.87.

(E) 4.4 g of 4-tert.butyl 1-(4-nitrobenzyl) 2(R)-isobutylsuccinate were dissolved in 50 ml of ethyl acetate and hydrogenated for 3.5 hours at room temperature and atmospheric pressure in the presence of 0.6 g of 5% palladium/carbon. The catalyst was removed by filtration and the solution was extracted three times with cold 2N hydrochloric acid. The organic layer was then washed with water and saturated sodium chloride solution and dried over anhydrous sodium sulfate. The solvent was removed by evaporation and the crude product was purified by chromatography on silica gel using chloroform for the elution. 2.0 g (72%) of 4-tert.butyl hydrogen 2(R)-isobutylsuccinate were obtained in the form of an oil. Rf (System C) 0.65.

(F) 7.14 g of 4-tert.butyl hydrogen 2(R)-isobutylsuccinate and 8.3 g of L-leucyl-L-alanine ethyl ester hydrochloride were dissolved in 50 ml of dimethylformamide and the mixture was cooled in an ice/salt bath. 4.22 g of hydroxybenzotriazole and 6.43 g of N,N'-dicyclohexylcarbodiimide were added, followed by 4 ml of N-ethylmorpholine. The mixture was left to warm to room temperature and then stirred overnight. Dicyclohexylurea was removed by filtration and the filtrate was evaporated to dryness. The residue was partitioned between 150 ml of ethyl acetate and 100 ml of water. The organic phase was washed in sequence twice with 50 of 5% citric acid solution each time, twice with 50 ml of saturated sodium hydrogen carbonate solution each time, once with 50 ml of water and once with 50 ml of saturated sodium chloride solution and then dried over anhydrous sodium sulfate. After removal of the solvent by evaporation, there were obtained 15 g of a solid. This solid was suspended in 20 ml of ethyl acetate, 50 ml of 4N hydrogen bromide in acetic acid were added and the mixture was stirred at room temperature for 45 minutes. The solvent was removed in vacuo to yield a gum which was treated several times with 100 ml portions of dry toluene and evaporated in vacuo each time. The residue was then dissolved in 75 ml of ethyl acetate and extracted three times with 100 ml of saturated sodium hydrogen carbonate solution each time. The combined aqueous extracts were acidified to pH 3 with 10% citric acid solutions and the product was extracted with two 150 ml portions of ethyl acetate. The organic phase was washed with water and saturated sodium chloride solution and then dried over anhydrous sodium sulfate. Removal of the solvent under reduced pressure yielded 8.3 g of [2(R)-isobutylsuccinyl]-L-leucyl-L-alanine ethyl ester as a solid. Thin-layer chromatography showed one major spot; Rf (chloroform/methanol 19:1) 0.24.

(G) 8.3 g of [2(R)-isobutylsuccinyl]-L-leucyl-L-alanine ethyl ester were dissolved in 80 ml of dry tetrahydrofuran and the solution was cooled to −15° C. 2.75 ml of N-ethylmorpholine were added, followed by 2.81 ml of isobutyl chloroformate. The mixture was stirred at −15° C. for 5 minutes and then 2.65 g of O-benzylhydroxylamine were added. The resulting solution was then stirred at −15° C. for 30 minutes and at room temperature for 1 hour. The solvent was removed by evaporation and the residue was partitioned between 150 ml of chloroform and 100 ml of water. The organic phase was washed in sequence with 10% citric acid solution, water, saturated sodium hydrogen carbonate solution and saturated sodium chloride solution and then dried over anhydrous sodium sulfate. After evaporation to dryness, there was obtained a solid which was recrystallized by dissolution in hot ethanol, adding ethyl acetate and cooling at 0° C. 6.5 g (61.5%) of [4-(N-benzylamino) 2(R)-isobutylsuccinyl]-L-leucyl-L-alanine ethyl ester of melting point 179°–181° C. were obtained. Rf (chloroform/methanol 19:1) 0.51.

EXAMPLE 14

0.23 g of [4-N-(benzyloxyamino) 2(R)-propylsuccinyl]-L-leucylglycine ethyl ester was dissolved in 10 ml of ethanol and hydrogenated for 1 hour in the presence of 0.1 g of 5% palladium/carbon. The catalyst was removed by filtration and the filtrate was evaporated to dryness. The solid was filtered off and washed with diethyl ether to give 0.17 g (89%) of [4-(N-hydroxyamino) 2(R)-propylsuccinyl]-L-leucylglycine ether ester. Rf (System A) 0.53.

The [4-(N-benzyloxyamino) 2(R)-proylsuccinyl]-L-leucylglycine ethyl ester used as the starting material was prepared as follows:

(A) 6.3 g of D-norvalic acid were heated under reflux in 100 ml of ethyl acetate in the presence of 7.43 ml of triethylamine and 6.99 ml of benzyl bromide for 2 hours. The mixture was washed in sequence with water, two 50 ml portions of 10% citric acid solution, water and saturated sodium chloride solution and then dried over anhydrous sodium sulfate. The solvent was removed by evaporation and the crude material was purified by chromatography on silica gel using for the elution 5% diethyl ether in n-hexane gradually increasing to 15% diethyl ether in n-hexane. There was obtained 6.94 g (63%) of D-norvalic acid benzyl ester a gum. Rf (diethyl ether/n-hexane 1:1) 0.4.

(B) In a manner analogous to that described in Example 13(B), 13(c) and 13(D), from D-norvalic acid benzyl ester there was prepared 4-tert.butyl 1-benzyl 2(R)-propylsuccinate. Rf (System A) 0.90.

(C) The benzyl group was removed from 4-tert.butyl 1-benzyl 2(R)-propylsuccinate by hydrogenation in isopropanol in the presence of 5% palladium/carbon. After filtration and evaporation of the filtrate there was obtained 4-tert.butyl hydrogen 2(R)-propylsuccinate as an oil. Rf (System A) 0.69.

(D) 0.98 g of 4-tert.butyl hydrogen 2(R)-propylsuccinate and 1.14 g of L-leucylglycine ethyl ester hydrochloride were dissolved in 25 ml of dry dimethylformamide and solution was cooled in an ice/salt bath. 0.61 g of hydroxybenzotriazole and 9.93 g of N,N'-dicyclohexylcarbodiimide were added, followed by 0.58 ml of N-ethylmorpholine. The mixture was left to stir overnight. Dicyclohexylurea was then removed by filtration and the filtrate was evaporated to dryness. The resulting gum was partitioned between ethyl acetate and water. The organic phase was washed in sequence with 10% citric acid solution, sodium hydrogen carbonate solution and saturated sodium chloride solution and then dried over sodium sulfate. The solvent was removed by evaporation and the crude product was chromatographed over silica gel using 2% methanol in chloroform for the elution to yield 1.1 g (59%) of [4-tert.butyl 2(R)-propylsuccinyl]-L-leucyl-glycine ethyl ester. Rf (chloroform/methanol 19:1) 0.62.

(E) 1.1 g of [4-tert.butyl 2(R)-propylsuccinyl]-L-leucylglycine ether ester were taken up in 7 ml of ethyl acetate and the solution was stirred at room temperature for 1 hour with 14 ml of 4N hydrogen bromide in acetic acid. The solvent was removed by evaporation and the resulting gum was taken up in 15 ml of ethyl acetate and extracted tree times with 25 ml of saturated sodium hydrogen carbonate solution each time. The combined aqueous extracts were acidified to about pH 3 with 2N hydrochloric acid. The free acid was extracted three times with 25 ml of ethyl acetate each time, washed with water and saturated sodium chloride solution and dried over anhydrous sodium sulfate. The solvent was removed by evaporation to yield 0.59 g (62%) [2(R)-propylsuccinyl]-L-leucylglycine ethyl ester as an oil which solidified upon leaving to stand. Rf (chloroform/methanol 9:1) 0.33.

(F) 0.54 g of [2(R)-propylsuccinyl]-L-leucylglycine ethyl ester was coupled with 0.184 g of O-benzylhydroxylamine by the mixed anhydride method as described in Example 13(G). After working-up as described in Example 13(G), there was obtained 0.45 g (64%) of [4-(N-benzyloxyamino) 2(R)-propylsuccinyl]-L-leucylglycine ethyl ester as a solid. Rf (chloroform/methanol 9:1) 0.61.

EXAMPLE 15

In a manner analogous to that described in Example 13, from 2(RS)-3(S)-isoleucic acid there was obtained [4-(N-hydroxyamino) 2(RS)-sec. butylsuccinyl]-L-leucylglycine ether ester. Rf (chloroform/methanol 9:1) 0.40.

EXAMPLE 16

0.491 g of [4-(N-benzyloxyamino) 2(R)-isobutylsuccinyl]-L-leucyl-L-alanine ethyl ester in 10 ml of ethanol, 8 ml of water and 2 ml of 1N sodium hydroxide solution was stirred at room temperature for 3 hours. The ethanol was removed by evaporation, the solution was diluted with 10 ml of water and extracted twice with 15 ml of chloroform each time. The aqueous solution was acidified with 2N hydrochloric acid and the resulting solid was filtered, washed with water and dried in vacuo. The resulting [4-(N-benzyloxyamino) 2(R)-isobutylsuccinyl]-L-leucyl-L-alanine was taken up in 10 ml of ethanol and hydrogenated for 2 hours in the presence of 5% palladium/carbon. The mixture was filtered, the filtrate was evaporated and the product was washed with diethyl ether and dried in vacuo. There was obtained 0.25 g (67%) of [4-(N-hydroxyamino) 2(R)-isobutylsuccinyl]-L-leucyl-L-alanine.

EXAMPLE 17

0.463 g of [4-(N-benzyloxyamino) 2(RS)-isobutylsuccinyl]-L-leucylglycine methyl ester in 5 ml of methanol was hydrogenated for 4 hours in the presence of 50 mg of 5% palladium/carbon. The mixture was filtered and the filtrate was evaporated to yield 0.335 g (90%) of [4-(N-hydroxyamino) 2(RS)-isobutylsuccinyl]-L-leucylglycine methyl ester as a foam.

The [4-(N-benzyloxyamino) 2(RS)-isobutylsuccinyl]-L-leucylglycine methyl ester used as the starting material was prepared as follows:

(A) 45.2 g of 4-tert.butyl hydrogen 2(RS)-isobutylsuccinate in 150 ml of dichloromethane was treated at 0° C. with a solution, cooled to 0° C., of 42.8 g of methyl L-leucinate hydrochloride and 30.0 ml of N-ethylmorpholine in 200 ml of dichloromethane. 31.8 g of hydroxybenzotriazone were added, followed by 44.4 g of N,N'-dicyclohexylcarbodiimide in 110 ml of dichloromethane. The mixture was stirred at 0° C. for 1 hour, left to stand at 4° C. overnight, filtered and evaporated. The residue was taken up in ethyl acetate and washed in sequence with water, 5% citric acid solution, water, 5% sodium hydrogen carbonate solution and saturated sodium chloride solution, dried over anhydrous magnesium sulfate and evaporated to give 71 g of [4-tert.butyl 2(RS)isobutylsuccinyl]-L-leucine methyl ester as a gel. Rf (n-hexane/ethyl acetate 2:1) 0.87.

(B) 64 g of [4-tert.butyl 2(RS)-isobutylsuccinyl]-L-leucine methyl ester in 130 ml of ethyl acetate were treated with 100 ml of 4N hydrogen bromide in acetic acid for 0.5 hour. The solvent was removed by evaporation and final traces of acetic acid were removed by the addition of 100 ml of toluene followed by evaporation, this procedure being carried out three times. The residue was taken up in 150 ml of ethyl acetate and extracted three times with 150 ml of 5% sodium hydrogen carbonate solution each time. The aqueous solutions were combined, acidified with 2N hydrochloric acid and the product was extracted twice with 200 ml of ethyl acetate each time. The solution was washed twice with 100 ml of saturated sodium chloride solution each time, dried over anhydrous magnesium sulfate and evaporated to give 37.1 g of [2(RS)-isobutyl-succinyl]-L-leucine methyl ester as an oil. Rf (System A) 0.58.

(C) A solution of 37.1 g of [2(RS)-isobutylsuccinyl]-L-luecine methyl ester in 200 ml of tetrahydrofuran at −12° C. was treated with 15.65 ml of N-ethyl-morpholine and 16.14 ml of isobutyl chloroformate and the mixture was stirred at −12° C. for 4 minutes. 15.2 g of O-benzylhydroxylamine were added and the mixture was stirred at 0° C. for 1 hour, left to stand at 0° C. for 64 hours and then evaporated. The residue was taken up in 200 ml of ethyl acetate, washed in succession with water, 5% citric acid solution, water and 5% sodium hydrogen carbonate solution, dried over anhydrous magnesium sulfate and evaporated to an oil. Chromatography on 500 g of silica gel using methanol/dichloromethane (1:24) for the elution yielded 35.5 g (71%) of [4-(N-benzyloxyamino) 2(RS)-isobutylsuccinyl]-L-leucine methyl ester as a mixture of isomers. Rf (chloroform/methanol 9:1) 0.30, 0.46.

(D) 35.5 g of [4-(N-benzyloxyamino) 2(RS)-isobutylsuccinyl]-L-leucine methyl ester in 200 ml of methanol and 180 ml of water were stirred at room temperature for 16 hours with 22 ml of 4N sodium hydroxides solution. The suspension was evaporated in order to remove the methanol, 200 ml of water were added and the mixture was extracted with ethyl acetate. The aqueous solution was acidified with 2N hydrochloric acid. The product was taken up in ethyl acetate, washed with water and saturated sodium chloride solution, dried over anhydrous magnesium sulfate and evaporated to yield 17.5 g (51%) of [4-(N-benzyloxyamino) 2(RS)-isobutylsuccinyl]-L-leucine as a foam.

The first ethyl acetate solution was washed with water and saturated sodium chloride solution, dried over anhydrous magnesium sufhate and evaporated to yield [4-(N-benzyloxyamino) 2(RS)-isobutylsuccinyl]-L-leucine methyl ester. This ester in 200 ml of methanol and 180 ml of water was stirred for 4 hours with 22 ml of 4N sodium hydroxide solution. Using the same working-up procedure as described in the preceding paragraph there were obtained an additional 13.2 g (39%) of [4-(N-benzyloxyamino) 2(RS)-isobutylsuccinyl]-L-leucine. The total yield was 30.7 g (90%).

(E) 2.07 g of [4-(N-benzyloxyamino) 2(RS)-isobutylsuccinyl]-L-leucine in 20 ml of tetrahydrofuran at 0° C. was treated with a solution, cooled to 0° C., of 0.63 g of methyl glycinate hydrochloride and 0.64 ml of N-ethylmorpholine in 10 ml of chloroform. 0.81 g of hydroxybenzotriazole and 1.13 g of N,N!-dicyclohexylcarbodiimide were added, the mixture was stirred at 0° C. for 1 hour, left to stand at 0° C. for 16 hours, filtered and evaporated. The residue was taken up in ethyl acetate and washed in sequence with 5% citric acid solution, water, 5% sodium hydrogen carbonate solution and saturated sodium chloride solution, dried over anhydrous magnesium sulfate and evaporated. Chromatography of the residue on 25 g of silica gel using ethyl acetate/hexane (1:1) for the elution yielded 1.9 g (82%) of [4-(N-benzyloxyamino) 2(RS)-isobutylsuccinyl]-L-leucylglycine methyl ester as a foam.

EXAMPLE 18

In a manner analogous to that described in Example 17, the following compounds were prepared:

[4-(N-hydroxyamino) 2(RS)-isobutylsuccinyl]-L-leucylsarcosine ethyl ester;

[4-(N-hydroxyamino) 2(RS)-isobutylsuccinyl]-L-leucyl-L-proline ethyl ester;

[4-(N-hydroxyamino) 2(RS)-isobutylsuccinyl]-L-leucyl-L-alanine isopropyl ester;

[4-(N-hydroxyamino) 2(RS)-isobutylsuccinyl]-L-leucine isopropylamide;

[4-(N-hydroxyamino) 2(RS)-isobutylsuccinyl]-L-leucine 2-oxopropylamide;

[4-(N-hydroxyamino) 2(RS)-isobutylsuccinyl]-L-leucine 2-methoxyethylamide;

[4-(N-hydroxyamino) 2(RS)-isobutylsuccinyl]-L-leucine 2,2-dimethoxyethylamide.

EXAMPLE 19

0.4 g of [N-formyl-N-benzyloxy 2(RS)-isobutyl-3-aminopropionyl]-L-leucylglycine ethyl ester in 20 ml of ethanol was hydrogenated for 0.75 hour in the presence of 5% palladium/carbon. The mixture was filtered, the filtrate was evaporated and the residue was dried in vacuo to yield 0.32 g (98%) of [N-formyl-N-hydroxy 2(RS)-isobutyl-3-aminopropionyl]-L-leucylglycine ethyl ester as a foam.

The [N-formyl-N-benzyloxy 2(RS)-isobutyl-3-aminopropionyl]-L-leucylglycine ethyl ester used as the starting material was prepared as follows:

(A) 2.85 g of isobutylacrylic acid and 10.9 g of O-benzylhydroxylamine were heated under reflux in 30 ml of methanol for 8 days. The solvent was removed by evaporation and the residue was dissolved in ethyl acetate and water. The organic layer was washed with 2N hydrochloric acid and water and then extracted six times with 30 ml of 5% sodium hydrogen carbonate solution each time. The aqueous solutions were combined, acidified with 2N hydrochloric acid and extracted with ethyl acetate. The ethyl acetate extract was washed with water and saturated sodium chloride solution, dried over anhydrous magnesium sulfate and evaporated to give an oil which soon crystallized. Trituration with petroleum yielded 1.92 g (35%) of N-benzyloxy 2(RS)-isobutyl-3-aminopropionic acid of melting point 73°–75° C. Rf (toluene/acetic acid 4:1) 0.52.

(B) 1.0 g of N-benzyloxy 2(RS)-isobutyl-3-amino-propionic acid in 10 ml of formic acid and 1 ml of acetic anhydride was stirred at room temperature for 2 hours and then evaporated. The residue was taken up in ethyl acetate, washed with water and saturated sodium chloride solution, dried over anhydrous magnesium sulfate and evaporated to yield 1.2 g (100%) of N-formyl-N-benzyloxy 2(RS)-isobutyl-3-aminopropionic acid as a gum. Rf (toluene/acetic acid 4:1) 0.39.

(C) In a manner analogous to that described in Example 1(D), from 1.2 g of N-formyl-N-benzyloxy 2(RS)-isobutyl-3-aminopropionic acid there were obtained 1.17 g (61%) of [N-formyl-N-benzyloxy 2(RS)-isobutyl-3-aminopropionyl]-L-leucylglycine ethyl ester as a mixture of an oil and crystals. Rf (ethyl acetate/n-hexane 7:3) 0.51.

EXAMPLE 20

0.12 g of $N^\alpha$-[4-(N-benzyloxyamino) 2(R)-isobutylsuccinyl]-$N^\epsilon$-(N-benzyloxycarbonylglycyl)-L-lysyl-L-alanine ethyl ester was dissolved in 20 ml of ethanol and hydrogenated in the presence of 0.1 g of 5% palladium/carbon and 0.172 ml of 1N hydrochloric acid for 1 hour. The catalyst was removed by filtration and the solvent was removed by evaporation to yield 70 mg (80%) of $N^\alpha$-[4-(N-hydroxyamino) 2(R)-isobutylsuccinyl]-$N^\epsilon$-glycyl-L-lysyl-L-alanine ethyl ester hydrochloride as a solid. Rf (System B) 0.3.

The $N^\alpha$-[4-(N-benzyloxyamino) 2(R)-isobutylsuccinyl]-$N^\epsilon$-(N-benzyloxycarbonylglycyl)-L-lysyl-L-alanine ethyl ester used as the starting material was prepared as follows:

(A) 13.3 g of $N^\alpha$-tert.butoxycarbonyl-$N^\epsilon$-benzyloxycarbonyl-L-lysine were dissolved in 100 ml of tetrahydrofuran and the solution was cooled to −20° C. 4.58 ml of isobutyl chloroformate and 4.48 ml of N-ethylmorpholine were then added. After stirring at −20° C. for 2 minutes 5.37 g of L-alanine ethyl ester hydrochloride and 4.48 ml of N-ethylmorpholine were added and the mixture was allowed to come to room temperature, whereafter it was stirred for 4 hours. The solvent was removed by evaporation and the residue was partitioned between 200 ml of ethyl acetate and 100 ml of water. The organic phase was washed in sequence twice with 25 ml of 10% citric acid solution each time, twice with 25 ml of saturated sodium hydrogen carbonate solution each time, once with 25 ml of water and once with 25 ml of saturated sodium chloride solution, dried and evaporated. The resulting gum crystallized from ethyl acetate/n-hexane. There were obtained 13 g (77%) of $N^\alpha$-tert.butoxycarbonyl-$N^\epsilon$-benzyloxycarbonyl-L-lysyl-L-alanine ethyl ester. Rf (chloroform/methanol 9:1) 0.73.

(B) 13 g of $N^\alpha$-tert.butoxycarbonyl-$N^\epsilon$-benzyloxycarbonyl-L-lysyl-L-analine ethyl ester were dissolved in 15 ml of 4N hydrogen chloride in ethyl acetate and the solution was stirred at room temperature for 0.5 hour. The solvent was removed in vacuo and the product was dried in a high vacuum to give 11.5 g (100%) of $N^\epsilon$-benzyloxycarbonyl-L-lysyl-L-alanine ethyl ester hydrochloride as a solid.

(C) 4.5 g of 4-tert.butyl hydrogen 2(R)-isobutylsuccinate were dissolved in a mixture of 20 ml of dimethylformamide and 20 ml of tetrahydrofuran. The solution was cooled to −20° C. and 2.5 ml of N-ethylmorpholine and 2.56 ml of isobutyl chloroformate were added. 8.13 g of $N^\epsilon$-benzyloxycarbonyl-L-lysyl-L-alanine ethyl ester hydrochloride were added after 2 minutes and subsequently 2.5 ml of N-ethylmorpholine were added. The mixture was stirred at room temperature for 4 hours and evaporated. The residue was taken up in ethyl acetate, washed in sequence with 10% citric acid solution, water, 5% sodium hydrogen carbonate solution and saturated sodium chloride solution, dried over anhydrous sodium sulfate and evaporated. There were obtained 13 g of crude product which was purified by chromatography on silica gel using chloroform for the elution. There were thus obtained 9.8 g (93%) of pure $N^\alpha$-[4-tert.butyl 2(R)-isobutylsuccinyl]-$N^\epsilon$-benzyloxycarbonyl-L-lysyl-L-alanine ethyl ester as a pale yellow oil. Rf (chloroform/methanol 9:1) 0.54.

(D) 5.65 g of $N^\alpha$-[4-tert.butyl 2(R)-isobutylsuccinyl]-$N^\epsilon$-benzyloxycarbonyl-L-lysyl-L-alanine ethyl ester were hydrogenated in 200 ml of ethanol in the presence of 500 mg of 5% palladium/carbon and 9.56 ml of 1N hydrochloric acid for 3 hours. The catalyst was removed by filtration and the filtrate was evaporated in vacuo to give 4.7 g (100%) of $N^\alpha$-[4-tert.butyl 2(R)-isobutylsuccinyl]-L-lysyl-L-alanine ethyl ester hydrochloride as a gum.

(E) 2.25 g of the foregoing hydrochloride salt and 0.953 g of N-benzyloxycarbonylglycine were dissolved in 5 ml of dimethylformamide and the solution was cooled in an ice/salt bath. 0.62 g of hydroxybenzotriazole and 0.94 g of N,N'-di-cyclohexylcarbodiimide were added, followed by 0.58 ml of N-ethylmorpholine. The mixture was stirred at room temperature overnight and dicyclohexylurea was then removed by filtration. Subsequently, the solvent was removed by evaporation and the resulting gum was partitioned between ethyl acetate and water. The organic phase was washed in sequence with 10% citric acid solution, saturated sodium hydrogen carbonate solution, water and saturated sodium chloride solution and then dried over anhydrous sodium sulfate. The solvent was removed in vacuo and the crude product was purified by chromatography on silica gel using chloroform and then 2% methanol in chloroform for the elution. 1.5 g (53%) of pure $N^\alpha$-[4-tert.butyl 2(R)-isobutylsuccinyl]-$N^\epsilon$-(N-benzyloxycarbonylglycyl)-L-lysyl-L-alanine ethyl ester were isolated. Rf (System A) 0.67.

(F) 1.5 g of $N^\alpha$-[4-tert.butyl 2(R)-isobutylsuccinyl]-$N^\epsilon$-(N-benzyloxycarbonylglycyl)-L-lysyl-L-alanine ethyl ester were dissolved in 10 ml of trifluoroacetic acid and the solution was stirred at room temperature for 1 hour. The solvent was removed in vacuo and the product was dried under a high vacuum for 5 hours over potassium hydroxide pellets. There were obtained 1.24 g (91%) of $N^\alpha$-[2(R)-isobutylsuccinyl]-$N^\epsilon$-(N-benzyloxycarbonylglycyl)-L-lysyl-L-alanine ethyl ester as a white solid.

(G) 1.24 g of $N^\alpha$-[2(R)-isobutylsuccinyl]-$N^\epsilon$-(N-benzyloxycarbonylglycyl)-L-lysyl-L-alanine ethyl ester and 0.26 g of O-benzylhydroxyl-amine were coupled in 15 ml of dimethylformamide using 0.283 g of hydroxybenzotriazole and 0.43 g of dicyclohexylarbodiimide in the presence of 0.24 g of N-ethylmorpholine. After stirring overnight the mixture was worked-up as described in paragraph (E) above. The crude product was purified by chromatography on silica gel using chloroform and 2% methanol in chloroform for the elution. There was obtained 0.78 g (65%) of $N^\alpha$-[4-(N-benzyloxyamino) 2(R)-isobutylsuccinyl]-$N^\epsilon$-(N-benzyloxycarbonylglycyl)-L-lysyl-L-alanine ethyl ester as a white solid. Rf (chloroform/methanol 19:1) 0.49; (System A) 0.68.

EXAMPLE 21

In a manner analogous to that described in Example 20, there was prepared $N^\alpha$-[4-(N-hydroxyamino) 2(R)-isobutylsuccinyl]-$N^\epsilon$-glycyl-L-lysine methylamide. Rf (System B) 0.19.

EXAMPLE 22

0.15 g of $N^\alpha$-[4-(N-benzyloxyamino) 2(R)-isobutylsuccinyl]-$N^\epsilon$-(4-benzyloxycarbonylbenzoyl)-L-lysyl-L-alanine ethyl ester was dissolved in 15 ml of dimethylformamide and hydrogenated in the presence of 0.1 g of 5% palladium/carbon for 1 hour. The catalyst was removed by filtration and the solvent was removed under reduced pressure. The residue was triturated with diethyl ether, filtered off and dried in vacuo to yield 80 mg (71%) of $N^\alpha$-[4-hydroxyamino) 2(R)-isobutylsuccinyl]$N^\epsilon$-(4-carboxybenzoyl)-L-lysyl-L-alanine ethyl ester as a solid. Rf (System B) 0.79.

The $N^\alpha$-[4-(N-benzyloxyamino) 2(R)-isobutylsuccinyl]-$N^\epsilon$-(4-benzyloxycarbonylbenzoyl)-L-lysyl-L-alanine ethyl ester used as the starting material was prepared as follows:

(A) $N^\epsilon$-[4-tert.butyl 2(R)-isobutylsuccinyl]-L-lysyl-L-alanine ethyl ester hydrochloride and 4-benzyloxycarbonylbenzoic acid were coupled in a manner analogous to that described in Example 20(E). The crude product obtained after working-up was purified by chromatography on silica gel using a gradient of chloroform up to 5% methanol in chloroform for the elution to give $N^\alpha$-[4-tert.butyl 2(R)-isobutylsuccinyl)-$N^\epsilon$-(4-benzyloxycarbonylbenzoyl)-L-lysyl-L-analine ethyl ester as a yellow oil. Rf (chloroform/methanol 9:1) 0.71.

(B) 2.9 g of $N^\alpha$-[4-tert.butyl 2(R)-isobutylsuccinyl)$N^\epsilon$-(4-benzyloxycarbonylbenzoyl)-L-lysyl-L-alanine ethyl ester were dissolved in 20 ml of trifluoroacetic acid and the solution was stirred at room temperature for 20 minutes. The solvent was removed by evaporation and the crude product was purified by chromatography on silica gel using 5% methanol in chloroform for the elution, there being obtained 0.735 g of $N^\alpha$-[2(R)-isobutylsuccinyl]-$N^\epsilon$-(4-benzyloxycarbonylbenzoyl)-L-lysyl-L-alanine ethyl ester. This was coupled with O-benzylhydroxylamine using dicyclohexylcarbodiimide/-hydroxybenzotriazole in a manner analogous to that described in Example 20(G). After working-up, the crude product was purified by chromatography on silica gel using and a gradient chloroform up to 5% methanol in chloroform for the elution. There was obtained b 0.6 g (72%) of $N^\alpha$-[4-(N-benzyloxyamino) 2(R)-isobutylsuccinyl]-$N^\epsilon$-(4-benzyloxycarbonylbenzoyl)-L-lysyl-L-alanine ethyl ester as a white solid. Rf (chloroform/methanol 19:1) 0.37.

EXAMPLE 23

0.16 g of $N^\alpha$-[4-(N-benzyloxyamino) 2(R)-isobutylsuccinyl]-$N^\epsilon$-(4-carboxybenzoyl)-L-lysyl-L-alanine was dissolved in 5–10 ml of dimethylformamide and hydrogenated in the presence of 0.1 g of 5% palladium/carbon for 1 hour. The catalyst was removed by filtration and the filtrate was evaporated to yield a solid which was triturated with diethyl ether, filtered and dried in vacuo. There was obtained 0.1 g (72%) of $N^\alpha$-[4-(N-hydroxyamino) 2(R)-isobutylsuccinyl]-$N^\epsilon$-(4-carboxybenzoyl)-L-lysyl-L-alanine as a solid. Rf (System B) 0.78.

The $N^\alpha$-[4-(N-benzyloxyamino) 2(R)-isobutylsuccinyl -$N^\epsilon$-(4-carboxybenzoyl)-L-lysyl-L-alanine used as the starting material was prepared as follows:

0.2 g of $N^\alpha$-[4-(N-benzyloxyamino) 2(R)-isobutylsuccinyl]-$N^\epsilon$-(4-benzyloxycarbonylbenzoyl)-L-lysyl-L-alanine ethyl ester was dissolved in 5 ml of dimethylformamide and stirred at room temperature in the presence of 0.55 ml of 1 N sodium hydroxide solution. After 2 hours the solvent was removed by evaporation and the residue was taken up in water and acidified to a pH of about 3 with 1N hydrochloric acid. The product was filtered, washed with water and diethyl ether and dried in vacuo to yield 0.16 g (82%) of $N^\alpha$[4-(N-benzyloxyamino) 2(R)-isobutylsuccinyl]-$N^\epsilon$-(4-carboxybenzoyl)-L-lysyl-L-alanine. Rf (System B) 0.85.

EXAMPLE 24

0.35 g of [4-(N-benzyloxyamino) 2(R)-isobutylsuccinyl]-3(RS)-aminolaurolactam was suspended in 15 ml of methanol and hydrogenated for 2 hours in the presence of 5% palladium/carbon. The mixture was filtered, the filtrate was evaporated and the residue was washed with diethyl ether to yield 0.27 g (95%) of [4-(N-hydroxyamino) 2(R)-isobutylsuccinyl]-3(RS)-aminolaurolactam as a solid of melting point 200°–205° C.

The [4-(N-benzyloxyamino) 2(R)-isobutylsuccinyl]-3(RS)-aminolaurolactam used as the starting material was prepared as follows:

(A) 19.7 g of laurolactam in 100 ml of chloroform were cooled to 0° C. 20.8 g of phosphorus pentachloride were added portionwise over a period of 40 minutes while keeping the temperature below 5° C. There was then added 0.2 g of iodine, followed by 16.0 g (0.2 mol) of bromine over a period of 20 minutes. The mixture was heated under reflux for 4 hours, cooled, evaporated and poured on to ice. The product was taken up in chloroform, washed with sodium hydrogen sulfate solution, dried over anhydrous magnesium sulfate and evaporated. Crystallization from chloroform/ n-hexane yielded 12.65 g (46%) of 3-bromolaurolactam of melting point 155°–157° C.

(B) 9.3 g of 3-bromolaurolactam and 8.6 g of sodium azide in 100 ml of dimethylformamide were heated at 80° C. for 64 hours and then evaporated. The residue was taken up in chloroform, washed with water, dried over anhydrous magnesium sulfate and evaporated to give the azide in the formed of a solid. This solid was taken up in 70 ml of ethanol and hydrogenated for 64 hours in the presence of 5% palladium/carbon. The solution was filtered and evaporated, and the residue was dissolved in chloroform. The product was extracted into water containing 17 ml of 2N hydrochloric acid. Evaporation, drying and crystallization from ethanol/diethyl ether yielded 4.9 g (58% of 3-aminolaurolactam hydrochloride as a white solid of melting point 251°-254° C.

(C) 1.73 g of 3-aminolaurolactam hydrochloride in 20 ml of dimethylformamide at 0° C was treated with 0.88 ml of N-ethylmorpholine. 1.6 g of 4-tert.-butyl hydrogen 2(R)-isobutylsuccinate, 1.14 g of hydroxybenzotriazole and 1.59 g of N,N'-dicyclohexylcarbodiimide were added and the mixture was stirred 0° C. for 1 hour and then left to stand at 0° C. overnight. The solution was filtered, the filtrate was evaporated and the residue was dissolved in ethyl acetate, washed in sequence with 5% citric acid solution, water, 5% sodium hydrogen carbonate solution and saturated sodium chloride solution, dried over anhydrous magnesium sulfate and evaporated to give an oil. The resulting crude [4-tert.butyl 2(R)-isobutylsuccinyl]-3(RS)-aminolaurolactam in 10 ml of ethyl acetate was treated for 0.5 hour with 10 ml of 4N hydrogen bromide in acetic acid and the mixture was then evaporated. Three 20 ml portions of toluene were added and the mixture was evaporated after each addition in order to remove traces of acetic acid. The residue, a foam, was dissolved in 20 ml of tetrahydrofuran and cooled to −12° C. 1.11 ml of N-ethylmorpholine and 0.84 ml of isobutyl chloroformate were added and the mixture was stirred at −12° C. for 4 minutes. 0.94 g of O-benzylhydroxylamine was added, the mixture was stirred at 0° C. for 1 hour and at room temperature for 1 hour and then evaporated to give a solid. The product was washed with water and diethyl ether and recrystallized from chloroform/diethyl ether to yield 1.4 g (42%)( of [4-(N-benzyloxyamino) 2(R)-isobutylsuccinyl]-3(RS)-aminolaurolactam as a white solid of melting point 215°-222° C.

EXAMPLE 25

In a manner analogous to that described in Example 24, there was prepared [4-(N-hydroxyamino) 2(R)-isobutylsuccinyl]-3(RS)-amino-octahydro-2H-azonin-2-one as a foam. Rf (System A) 0.44.

EXAMPLE 26

0.4 g of [4-(N-benzyloxyamino) 3(S)-methyl-2(R)-isobutylsuccinyl]-L-leucylglycine ethyl ester in 10 ml of ethanol was hydrogenated for 2 hours in the presence of 5% palladium/carbon. The mixture was filtered.

The filtrate was evaporated and the residue was re-evaporated from dichloromethane to give 0.28 g (86%) of [4-(N-hydroxyamino) 3(S)-methyl-2(R)-isobutylsuccinyl]-L-leucylglycine ethyl ester in the form of a pink solid, Rf (System A) 0.56.

The [4-(N-benzyloxyamino)3(S)-methyl-2(R)-isobutylsuccinyl]-L-leucylglycine ethyl ester used as the starting material was prepared as follows:

(A) 1-Benzyl 4-tert.butyl 3-tert.butyloxycarbonyl-2(S)-methylsuccinate was prepared from benzyl S-lactate in a manner analogous to that described in Example 13(B). This material contained 13% of di-tert.butyl malonate.

(B) 11.77 g of crude 1-benzyl 4-tert.butyl 3-tert.-butyloxycarbonyl-2(S)-methylsuccinate in 100 ml of dimethylformamide was treated with 1.01 g of 80% sodium hydride. After 0.25 hour, 3.86 ml of isobutyl iodide were added and the mixture was heated at 80° C. for 2 hours. The same quantity of reagents were added and the heating at 80° C. was continued for an additional 2 hours. The mixture was cooled and evaporated, and the residue was dissolved in ethyl acetate. The ethyl acetate solution was washed with water and saturated sodium chloride solution, dried over anhydrous magnesium sulfate and evaporated to give a yellow oil. Chromatography on 250 g of silica gel using ethyl acetate/n-hexane (1:15) for the elution gave 8.76 g (74%) of 1-benzyl 4-tert.butyl 3-tert.-butyloxycarbonyl 3-isobutyl-2(S)-methylsuccinate as an oil. Rf (ethyl acetate/n-hexane 1:9) 0.70.

(C) 8.76 g of 1-benzyl 4-tert.butyl 3-tert.butyloxycarbonyl 3-isobutyl-2(S)-methylsuccinate in 10 ml of trifluoroacetic acid were stirred at room temperature for 1 hour and then evaporated, final traces of trifluoroacetic acid being removed by adding three 20 ml portions of toluene and evaporating the mixture each time. The residue was taken up in toluene, the solution was heated under reflux for 3 hours and then evaporated to give an oil. The oil was taken up in ethyl acetate, the solution was extracted three times with 50 ml of sodium hydrogen carbonate solution each time, the aqueous phase was acidified with 2N hydrochloric acid and extracted with ethyl acetate. The organic phase was washed with water and saturated sodium chloride solution, dried over anhydrous magnesium sulfate and evaporated to yield 2.55 g (45%) of 4-benzyl hydrogen 2(R)-isobutyl-3(S)-methylsuccinate as an oil. Rf (System A) 0.60.

(D) 1.76 g of 4-benzyl hydrogen 2(R)-isobutyl-3(S)-methylsuccinate were coupled to L-leucylglycine ethyl ester hydrobromide by the hydroxybenzotriazole/dicyclohexylcarbodiimide method as described in Example 1(D). Chromatography on 60 g of silica gel using ethyl acetate/n-hexane (4:6) for the elution yielded 1.4 g (47%) of [4-benzyl 3(S)-methyl-2(R)-isobutylsuccinyl]-L-leucylglycine ethyl ester as an oil. Rf (ethyl acetate/n-hexane 1:1) 0.53.

1.32 g of [4-benzyl 3(S)-methyl-2(R)-isobutylsuccinyl]-L-leucylglycine ethy ester in 20 ml of dimethylformamide were hydrogenated for 4 hours in the presence of 0.15 g of 5% palladium/carbon. The mixture was filtered, the filtrate was cooled to −12° C., 0.35 ml of N-ethylmorpholine and 0.36 ml of isobutyl chloroformate were added and the mixture was stirred at −12° C. for 4 minutes. 0.34 g of O-benzylhydroxylamine was added, the mixture was stirred at 0° C. for 2 hours and the solvent was then removed by evaporation. The residue was taken up in chloroform, washed in sequence with 5% citric acid solution, water, 5% sodium hydrogen carbonate solution and saturated sodium chloride solution, dried over anhydrous magnesium sulfate and evaporated to give a solid. Chromatography on 30 g of silica gel using chloroform for the elution gave 0.45 g (33%) of [4-(N-benzyloxyamino) 3(S)-methyl-2(R)-isobutylsuccinyl]-L-leucylglycine ethyl ester as a solid.

EXAMPLE 27

In a manner analogous to that described in Example 26, from L-lysine there was prepared [4-(N-hydroxyamino) 3(S)-phthaloylaminobutyl-2(R)-isobutylsuccinyl]-L-leucylglycine ethyl ester as a solid of melting point 197° C. (decomposition). Rf (System A) 0.64.

EXAMPLE 28

In a manner analogous to that described in Example 19, there was prepared [N-formyl-N-hydroxy 2(RS)-isobutyl-3-aminopropionyl]-L-leucyl-L-alanine ethyl ester and [N-formyl-N-hydroxy 2(RS)-isobutyl-3-aminopropinyl]-L-leucine methylamide as a foam.

The following Examples illustrate pharmaceutical preparations containing the hydroxylamine derivatives of formula I provided by the invention:

EXAMPLE A

Tablets containing the following ingredients may be produced in a conventional manner:

| Ingredient | Per tablet |
|---|---|
| Hydroxylamine derivative of formula I | 10.0 mg |
| Lactose | 125.0 mg |
| maize starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredient | Per capsule |
|---|---|
| Hydroxylamine derivative of formula I | 10.0 mg |
| Lactose | 165.0 mg |
| Maize starch | 20.0 mg |
| Talc | 5.0 mg |
| Capsule fill weight | 200.0 mg |

We claim:
1. A compound of the formula

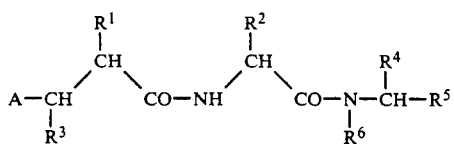

wherein
A is a group of the formula HN (OH)—CO— or HCO—N(OH)—;
$R^1$ is $C_2$–$C_5$-alkyl;
$R^2$ is isoproyl, isobutyl, benzyl, p-hydroxybenzyl, p-methoxybenzyl, hydroxymethyl, 1-hydroxyethyl, protected hydroxymethyl or 1-hydroxyethyl, mercaptomethyl, protected mercaptomethyl, 2-(methylthio) ethyl, carboxymethyl, 2-carboxyethyl, protected carboxymethyl or 2-carboxyethyl, 3-quanidinoproyl, 4-aminobutyl or protected 3-quanidinopropyl or 4-aminobutyl;
$R^3$ is hydrogen, amino, hydroxy, mercapto, $C_1$–$C_6$-alkyl, $C_1$–$C_6$-alkyl, $C_1$–$C_6$-alkylamino, $C_1$–$C_6$-alkylthio, aryl-($C_1$–$C_6$), amino-($C_1$–$C_6$-alkyl), protected amino-($C_1$–$C_6$-alkyl), hydroxy-($C_1$–$C_6$-alkyl), protected hydroxy-($C_1$–$C_6$-alkyl), mercapto-($C_1$–$C_6$alkyl), protected mercapto-($C_1$–$C_6$-alkyl), carboxy-($C_1$–$C_6$-alkyl) or protected carboxy-($C_1$–$C_6$-alkyl);

$R^4$ is hydrogen or methyl;
$R^5$ is $C_1$–$C_6$-alkoxy-$C_1$–$C_6$-alkyl, di ($C_1$–$C_6$-alkoxy)-methylene, carboxyl, ($C_1$–$C_6$-alkyl)carbonyl, ($C_1$–$C_6$-alkoxy)carbonyl, arylmethy oxycarbonyl, ($C_1$–$C_6$-alkyl)aminocarbonyl or arylaminocarbonyl group; and
$R^6$ is hydrogen or methyl or
$R^2$ and $R^4$ together represent a group of the formula —$(CH_2)_n$ in which n stands for a number from 4 to 11; or
$R^4$ and $R^6$ together represent trimethylene; or a pharmaceutically acceptable salt of a compound which is acidic or basic, and wherein the hydroxy protecting group is selected from the group consisting of tert.butyl, benzyl and tetrahydropyranyl;
the mercapto protecting group is selected from the group consisting of tert.butyl and benzyl;
the amino protecting group is selected from the group consisting of tert.butoxycarbonyl, benzyloxycarbonyl, formyl, trityl, trifluoroacetyl, 2-(biphenylyl)-isopropoxycarbonyl isobornyloxycarbonyl and an acyl group derived from phthalic acid, terephthalic acid, glycine or alanine;
the protected carboxy group is a carboxy group protected in the form of a methyl, ethyl, tert.butyl or benzyl ester or in the form of an amide, N-($C_1$–$C_6$-alkyl)amine, N,N-di($C_1$–$C_6$-alkyl) amide, N-arylamide, N-(carboxymethyl)amide or N-(1-carboxyethyl) amide; and
aryl is selected from the group consisting of unsubstituted phenyl and phenyl substituted with one or more substituents selected from the group consisting of $C_1$–$C_6$-alkyl, $C_1$–$C_6$-alkoxy, halogen and trifluoromethyl.

2. A compound in accordance with claim 1, wherein $R^1$ is $C_3$- or $C_4$-alkyl.

3. A compound in accordance with claim 2, wherein $R^1$ is n-propyl, isobutyl or sec.butyl.

4. A compound in accordance with claim 3, wherein $R^2$ is isopropyl, isobutyl, p-methoxybenzyl, or protected 4-aminobutyl.

5. A compound in accordance with claim 4, wherein $R^2$ is p-methoxybenzyl, 4-tert.butoxycarbonyl-aminobutyl, 4-glycylamino-butyl or 4-(4-carboxybenzoylamine)-butyl.

6. A compound in accordance with claim 5, wherein $R^3$ is hydrogen, methyl or protected 4-aminobutyl.

7. A compound in accordance with claim 6, wherein $R^3$ is 4-phthaloylamino-butyl.

8. A compound in accordance with claim 7, wherein $R^4$ is hydrogen or methyl, or $R^2$ and $R^4$ taken together are a group of the formula —$(CH_2)_n$—in which n is a number from 5 to 9.

9. A compound in accordance with claim 8, wherein $R^4$ is hydrogen or methyl and $R^5$ is hydrogen, $C_1$–$C_6$-alkyl, $C_1$–$C_6$-alkoxy-$C_1$–$C_6$-alkyl, di($C_1$–$C_6$-alkoxy)-methylene, carboxyl or ($C_1$–$C_6$-alkoxy)carbonyl.

10. A compound in accordance with claim 9, wherein $R^5$ is carboxyl or ($C_1$–$C_6$-alkoxy)carbonyl.

11. A compound in accordance with claim 10, wherein $R^5$ is ethoxycarbonyl.

12. A compound in accordance with claim 8, wherein $R^2$ and $R^4$ taken together are a group of the formula —$(CH_2)_n$— in which n is a number from 5 to 9 and $R^5$ is hydrogen.

13. A compound in accordance with claim 11 wherein $R^6$ is hydrogen.

14. A compound in accordance with claim 1, herein $R^1$ is n-propyl, isobutyl or sec.butyl, $R^2$ is isopropyl, isobutyl, p-methoxybenzyl, 4-tert.butoxycarbonylamino-butyl, 4-glycylamino-butyl or 4-(4-carboxybenzoylamino)-butyl, $R^3$ is hydrogen, methyl or 4-phthaloylamino-butyl, $R^4$ is hydrogen or methyl, $R^5$ is carboxyl or ethoxycarbonyl and $R^6$ is hydrogen or $R^2$ and $R^4$ taken together are a group of the formula —$(CH_2)_n$— in which n is a number from 5 to 9, $R^5$ is hydrogen and $R^6$ is hydrogen.

15. A compound in accordance with claims 1, 12, 13 and 14, wherein the carbon atom to which $R^1$ is attached has the (R)-configuration, the carbon atom to which $R^2$ is attached has the (L)-configuration, the stereochemistry at the carbon atom to which $R^3$ is attached has the groups in these same orientation as (S) when $R^3$ is $C_1$–$C_6$-alkyl and the carbon atom to which $R^4$ is attached has the (S)-configuration when $R^4$ is methyl and $R^5$ is carboxyl, ($C_1$–$C_6$-alky)carbonyl, arylmethoxycarbonyl, ($C_2$–$C_6$-alkyl) aminocarbonyl or arylcarbonylamino.

16. A compound in accordance with claim 1, [4-(N-Hydroxyamino) 2(R)-isobutylsuccinyl]-L-leucylglycine ethyl ester.

17. A compound in accordance with claim 1, [4-(N-Hydroxyamino) 2(R)-isobutylsuccinyl]-L-leucyl-L-alanine ethyl ester.

18. A compound in according with claim 1, [N-Formyl-N-hydroxy 2(RS)-isobutyl-3-aminopropionyl]-L-leucylglycine ethyl ester.

19. A compound in accordance with claim 1, $N^\alpha$-[4-(N-Hydroxylamino) 2(R)-isobutylsuccinyl]-$N^\epsilon$-glycyl-L-lysyl-L-alanine ethyl ester.

20. A compound in accordance with claim 1, [4-(N-Hydroxyamino) 2(R)-isobutylsuccinyl]-3(RS)-aminolaurolactam.

21. A compound in accordance with claim 1, [4-(N-Hydroxyamino) 3(S)-phthaloylaminobutyl-2(R)-isobutylsuccinyl]-L-leucylglycine ethyl ester.

22. A compound selected from the group consisting [N-formyl-N-hydroxy 2(RS)-isobutyl-3-aminopropionyl]-L-leucyl-L-alanine ethyl ester or
[N-formyl-N-hydroxy 2(RS)-isobutyl-3-aminopropionyl]-L-leucine methylamide.

23. A compound of the formula

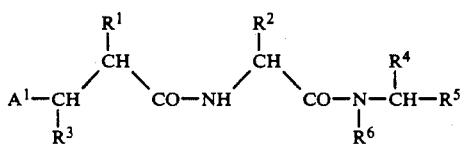

wherein
$A^1$ is a group of the formula HN($R^7$)—CO— or HCo—N($R^7$)—;
$R^7$ is benzyloxy, tetrahydropyranyloxyl, benzydryloxyl, trityloxy or tert.butoxy;
$R^1$ is $C_2$–$C_5$-alkyl;
$R^2$ is isopropyl, isobutyl, benzyl, p-hydroxybenzyl, p-methoxybenzyl, hydroxymethyl, 1-hydroxyethyl, protected hydroxymethyl or 1-hydroxyethyl, mercaptomethyl, protected mercaptomethyl, 2-(methylthio)ethyl, carboxymethyl, 2-carboxyethyl, protected carboxymethyl or 2-carboxyethyl, 3-quanidinopropyl, 4-aminobutyl or protected 3-quanidinopropyl or 4-aminobutyl;
$R^3$ is hydrogen, amino, hydroxy, mercapto, $C_1$–$C_6$-alkyl, $C_1$–$C_6$-alkoxy, $C_1$–$C_6$-alkylamino, $C_1$–$C_6$-alkylthio, aryl-($C_1$–$C_6$alkyl) amino ($C_1$–$C_6$-alkyl), protected amino-($C_1$–$C_6$-alkyl), hydroxy-($C_1$–$C_6$alkyl), protected hydroxy—($C_1$–$C_6$-alkyl), mercapto-($C_1$–$C_6$-alkyl), protected mercapto-($C_1$–$C_6$-alkyl), carboxy-($C_1$–$C_6$-alkyl) or protected carboxyl($C_1$–$C_6$-alkyl);
$R^4$ is hydrogen or methyl;
$R^5$ is $C_1$–$C_6$-aloxy-$C_1$–$C_6$-alkyl, di ($C_1$–$C_6$-alkoxy)-methylene, carboxyl, ($C_1$–$C_6$-alkyl)-carbonyl, ($C_1$–$C_6$-alkoxy)carbonyl, arylmeth oxycarbonyl, ($C_1$–$C_6$-alkyl)aminocarbonyl or arylaminocarbonyl group; and
$R^6$ is hydrogen or methyl or
$R^2$ and $R^4$ together represent a group of the formula —$(CH_2)_n$ in which n stands for a number from 4 to 11; or
$R^4$ and $R^6$ together represent trimethylene; and wherein the hydroxy protecting group is selected from the group consisting of tert.butyl, benzyl and tetrahydropyranyl;
the mercapto protecting group is selected from the group consisting of tert.butyl and benzyl;
the amino protecting group is selected from the group consisting of tert.butoxycarbonyl, benzyloxycarbonyl, formyl, trityl, trifluoroacetyl, 2-(biphenylyl)-isopropoxycarbonyl, isobornyloxycarbonyl and acyl group derived from phthalic acid, terephthalic acid, glycine or alanine;
the protected carboxy group is a carboxy group protected in the form of a methyl, ethyl, tert.butyl or benzyl ester or in the form of an amide, N-($C_1$–$C_6$-alkyl) amide, N,N-di ($C_1$–$C_6$-alkyl) amide, N-arylamide, N-(carboxymethyl)-amide, or N-(1-carboxyethyl) amide; and
aryl is selected from the group consisting of unsubstituted phenyl and phenyl substituted with one or more substituents selected from the group consisting of ($C_1$–$C_6$alkyl) $C_1$–$C_6$-alkoxy, halogen and trifluoromethyl.

24. A compound in accordance with claim 23, [4-(N-benzyloxyamino) 2(R)-isobutylsuccinyl]-L-leucyl-L-alanine ethyl ester.

25. A compound in accordance with claim 23, [4-(N-benzyloxyamino) 2(R)-isobutylsuccinyl]-3(RS)-aminolaurolactam.

26. A compound in accordance with claim 23, $N^\alpha$-[4-(N-benzyloxyamino) 2(R)-isobutylsuccinyl]-$N^\epsilon$-(N-benzyloxycarbonylglycyl)-L-lysyl-L-alanine ethyl ester.

27. A compound selected from the group consisting of:
[4-(N-Hydroxyamino) 2(RS)-isobutylsuccinyl]-L-leucylglycine ethyl ester;
[4-(N-hydroxyamino) 2(RS)-isobutylsuccinyl]-L-leucylglycine isopentylamide;
[4-(N-hydroxyamino) 2(RS)-isobutylsuccinyl]-L-valylglycine ethylamide;
[4-(N-hydroxyamino) 2(RS)-isobutylsuccinyl]-L-leucylglycine ethylamide.
$N^\alpha$-[4-(N-hydroxyamino) 2(RS)-isobutylsuccinyl]-$N^\epsilon$-tert.butoxycarbonyl-L-lysylglycine ethylaminde;
[4-(N-hydroxyamino) 2(RS)-isobutylsuccinyl]-O-methyl-L-tyrosinylglycine ethyl ester;
[4-(N-hydroxyamino) 2(RS)-isobutylsuccinyl]-O-methyl-L-tyrosinylglycine ethylamide;
[4-(N-hydroxyamino) 2(RS)-isobutylsuccinyl]-L-leucyl-L-alanine ethyl ester;

[4-(N-hydroxyamino) 2(RS)-isobutylsuccinyl]-L-leucylglycine isopentyl ester;
[4-(N-hydroxyamino) 2(R)-propylsuccinyl]-L-leucylglycine ether ester;
[4-(N-hydroxyamino) 2(RS)-sec.butylsuccinyl]-L-luecylglycine ethyl ester;
[4-(N-hydroxyamino) 2(R)-isobutylsuccinyl]-L-leucyl-L-alanine;
[4-(N-hydroxyamino) 2(RS)-isobutylsuccinyl]-L-leucylgylcine methyl ester;
[4-(N-hydroxyamino) 2(RS)-isobutylsuccinyl]-L-leucylsarconsine ethyl ester;
[4-(N-hydroxyamino) 2(RS)-isobutylsuccinyl]-L-leucyl-L-proline ethyl ester;
[4-(N-hydroxyamino) 2(RS)-isobutylsuccinyl]-L-leucine-L-alanine isopropyl ester;
[4-(N-hydroxyamino) 2(RS)-isobutylsuccinyl]-L-leucine-2-oxopropylamide;
[4-(N-hydroxyamino) 2(RS)-isobutylsuccinyl]-L-leucine 2-methoxyethylamide;
[4-(N-hydroxyamino) 2(RS)isobutylsuccinyl]-L-leucine 2,2-dimethoxyethylamide;
$N^\alpha$-[4-(N-hydroxyamino) 2(R)-isobutylsuccinyl]-$N^\epsilon$-glycyl-L-lysine methylamide;
$N^\alpha$-[4-(N-hydroxyamino) 2(R)-isobutylsuccinyl]-$N^\epsilon$-(4-carboxybenzoyl)-L-lysyl-L-alanine ethyl ester;
$N^\alpha$-[4-(N-hydroxyamino) 2(R)-isobutylsuccinyl]-$N^\epsilon$-(4-carboxybenzoyl)-L-lysyl-L-alanine;
[4-(N-hydroxyamino) 2(R)-isobutylsuccinyl]-3(RS)-aminooctahydro-2H-azonin-2-one and
[4-(Nhydroxyamino) 3(S)-methyl-2(R)-isobutylsuccinyl]-L-leucylglycine ethyl ester.

28. A pharmaceutical composition comprising an effective amount of a compound of the formula

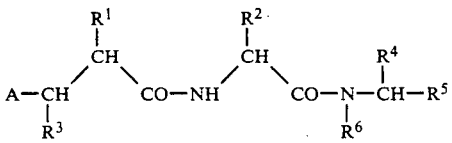

wherein
A is a group of the formula NH(OH)—CO— or HCO—N(OH—;
$R^1$ is $C_2$–$C_5$-alkyl;
$R^2$ is isopropyl, isobutyl, benzyl, p-hydroxybenzyl, p-methoxybenzyl, hydroxymethyl, 1-hydroxyethyl, protected hydroxymethyl or 1-hydroxyethyl, mercaptomethyl, protected mercaptomethyl, 2-(methylthio) ethyl, carboxymethyl, 2-carboxyethyl, protected carboxymethyl or 2carboxyethyl, 3-guanidinopropyl, 4-aminobutyl or protected 3-guanidinopropyl or 4-aminobutyl;
$R^3$ is hydrogen, amino, hydroxy, mercapto, $C_1$–$C_6$-alkyl, $C_1$–$C_6$-alkoxy, $C_1$–$C_6$-alkylamino, $C_1$–$C_6$-alkylthio, aryl-($C_1$–$C_6$-alkyl) amino-($C_1$–$C_6$-alkyl), protected amino-($C_1$–$C_6$-alkyl), hydroxy-($C_1$–$C_6$-alkyl), protected hydroxy-($C_1$–$C_6$-alkyl), mercapto-($C_1$–$C_6$-alkyl), protected mercapto-($C_1$–$C_6$-alkyl), carboxy-($C_1$–$C_6$-alkyl) or protected carboxy-($C_1$–$C_6$-alkyl);
$R^4$ is hydrogen or methyl;
$R^5$ is $C_1$–$C_6$-alkoxy-$C_1$–$C_6$-alkyl, di($C_1$–$C_6$-alkoxy)-methylene, carboxyl, ($C_1$–$C_6$-alkyl)-carbonyl, ($C_1$–$C_6$-alkoxy)-carbonyl, arylmeth oxycarbonyl, ($C_1$–$C_6$-alkyl)aminocarbonyl or arylaminocarbonyl group; and
$R^6$ is hydrogen or methyl or $R^2$ and $R^4$ together represent a group of the formula —$(CH_2)_n$ in which n stands for a number from 4 to 11; or
$R^4$ and $R^6$ taken together are trimethylene; or a pharmaceutically acceptable salt of a compound which is acidic or basic, and an inert carrier, and wherein the hydroxy protecting group is selected from the group consisting of tert.butyl, benzyl and tetrahydropyranyl;
the mercapto protecting group is selected from the group consisting of tert.butyl and benzyl;
the amino protecting group is selected from the group consisting of tert.butoxycarbonyl, benzyloxycarbonyl, formyl, trityl, trifluoroacetyl, 2-(biphenylyl)-isopropoxycarbonyl, isobornyloxycarbonyl and an acyl group derived from phthalic acid, terephthalic acid, glycine or alanine;
the protected carboxy group is a carboxy group protected in the form of a methyl, ethyl, tert.butyl or benzyl ester or in the form of an amide, N-$C_1$–$C_6$-alkyl amide, N,N-di($C_1$–$C_6$-alkyl) amide, N-arylamide, N-(carboxymethyl)-amide, or N-(1-carboxyethyl)amide; and aryl is selected from the group consisting of unsubstituted phenyl and phenyl substituted with one or more substituents selected from the group consisting of $C_1$–$C_6$-alkyl, $C_1$–$C_6$-alkoxy, halogen and trifluoromethyl.

29. A pharmaceutical composition in accordance with claim 28, wherein $R^1$ is n-propyl, isobutyl or sec.-butyl, $R^2$ is isopropyl, isobutyl, p-methoxybenzyl, 4-tert.butoxycarbonylamino-butyl, 4-glycylaminobutyl or 4-(4-carboxybenzoylamino)-butyl, $R^3$ is hydrogen, methyl or 4-phthaloyl-amino-butyl, $R^4$ is hydrogen or methyl, $R^5$ is a carboxyl or ethoxycarbonyl and $R^6$ is hydrogen or $R^2$ and $R^4$ taken together are a group of the formula —$(CH_2)_n$— in which n is a number from 5 to 9, $R^5$ is hydrogen and $R^6$ is hydrogen.

30. A pharmaceutical composition in accordance with claim 28, wherein the carbon atom to which $R^1$ is attached has the (R)-configuration, the carbon atom to which $R^2$ is attached has the (L)-configuration, the stereochemistry at the carbon atom to which $R^3$ is attached has the groups in the same orientation as (S) when $R^3$ is $C_1$–$C_6$-alkyl and the carbon atom to which $R^4$ is attached has the (S)-configuration when $R^4$ is methyl and $R^5$ i carboxyl, ($C_1$–$C_6$-alkoxy)carbonyl, arylmethoxycarbonyl, ($C_1$–$C_6$-alkyl)aminocarbonyl or arylcarbonylamino.

31. A pharmaceutical composition in accordance with claim 28, wherein the compound is [4-(N-Hydroxyamino) 2(R)-isobutylsuccinyl]-L-leucylglycine ethyl ester.

32. A pharmaceutical composition in accordance with claim 28, wherein the compound is [4-(N-Hydroxyamino) 2(R)-isobutylsuccinyl]-L-leucyl-L-alanine ethyl ester.

33. A pharmaceutical composition in accordance with claim 28, wherein the compound is [N-Formyl-N-hydroxy 2(RS)-isobutyl-3-aminopropionyl]-L-leucylglycine ethyl ester.

34. A pharmaceutical composition in accordance with claim 28, wherein the compound is $N^\alpha$-[4-(N-Hydroxyamino)2(R)-isobutylsuccinyl]-$N^\epsilon$glycyl-L-lysyl-L-alanine ethyl ester.

35. A pharmaceutical composition in accordance with claim 28, wherein the compound is [4-(N-Hydroxyamino) 2(R)-isobutylsuccinyl]-3(RS)-aminolaurolactam.

36. A pharmaceutical composition in accordance with claim 28, wherein the compound is [4-(N-hydroxyamino) 3(S)-phthaloylaminobutyl-2(R)-isobutylsuccinyl]-L-leucylglycine ethyl ester.

* * * * *

UNITED STATES PATENT AND TRADEMARK OFFICE
CERTIFICATE OF CORRECTION

PATENT NO. : 4,996,358

DATED : February 26, 1991

INVENTOR(S) : Balraj Krishan Handa, William Henry Johnson and Peter James Machin It is certified that error appears in the above-identified patent and that said Letters Patent is hereby corrected as shown below:

Claim 1, Column 27, line 53, "isoproyl" should be --- isopropyl --- .

Claim 1, Column 27, line 59, "3-quanidinoproyl" should be --- 3-guanidinopropyl --- .

Claim 1, Column 27, line 62, "$C_1$-$C_6$-alkyl," should be --- $C_1$-$C_6$-alkoxy --- .

Claim 1, Column 28, line 4, "arylmethy oxycarbonyl" should be --- arylmethoxycarbonyl --- .

Claim 1, Column 28, line 28, "alkyl)amine" should be --- alkyl)amide --- .

Claim 15, Column 29, line 19, "($C_1$-$C_6$-alkyl)" should be --- ($C_1$-$C_6$-alkoxy) --- .

Claim 23, Column 29, line 56 and 57, "benzydryloxyl," should be --- benzhydryloxy --- .

Claim 27, Column 31, line 6, "luecylglycine" should be --- leucylglycine --- .

UNITED STATES PATENT AND TRADEMARK OFFICE
CERTIFICATE OF CORRECTION

PATENT NO. : 4,996,358

DATED : February 26, 1991

INVENTOR(S) : Balraj Krishan Handa, William Henry Johnson and Peter James Machin It is certified that error appears in the above-indentified patent and that said Letters Patent is hereby corrected as shown below:

Claim 27, Column 31, line 31, "(Nhydroxyamino)" should be --- (N-hydroxyamino) --- .

Claim 30, Column 32, line 42, "i" should be --- is --- .

Signed and Sealed this

Third Day of August, 1993

Attest:

MICHAEL K. KIRK

Attesting Officer

Acting Commissioner of Patents and Trademarks